US012686723B2

(12) United States Patent
Li et al.

(10) Patent No.: US 12,686,723 B2
(45) Date of Patent: Jul. 21, 2026

(54) ANTI-BCMA ANTIBODY, PHARMACEUTICAL COMPOSITION OF SAME, AND APPLICATIONS THEREOF

(71) Applicant: Shanghai Acemab Corporation Ltd., Shanghai (CN)

(72) Inventors: Jianliang Li, Xiangtan (CN); Seeheng Wong, Xiangtan (CN); Junxia Zhang, Xiangtan (CN); Meng Tian, Xiangtan (CN); Wei Cai, Xiangtan (CN)

(73) Assignee: Shanghai Acemab Corporation Ltd., Shanghai (CN)

(*) Notice: Subject to any disclaimer, the term of this patent is extended or adjusted under 35 U.S.C. 154(b) by 912 days.

(21) Appl. No.: 17/904,216

(22) PCT Filed: Feb. 9, 2021

(86) PCT No.: PCT/CN2021/076319
§ 371 (c)(1),
(2) Date: Aug. 12, 2022

(87) PCT Pub. No.: WO2021/160133
PCT Pub. Date: Aug. 19, 2021

(65) Prior Publication Data
US 2023/0242656 A1 Aug. 3, 2023

(30) Foreign Application Priority Data
Feb. 13, 2020 (CN) .......................... 202010090567.8

(51) Int. Cl.
*C07K 16/28* (2006.01)
*C07K 14/705* (2006.01)
*A61K 39/00* (2006.01)

(52) U.S. Cl.
CPC .... *C07K 16/2878* (2013.01); *C07K 14/70578* (2013.01); *A61K 2039/505* (2013.01); *C07K 2317/73* (2013.01)

(58) Field of Classification Search
None
See application file for complete search history.

(56) References Cited

U.S. PATENT DOCUMENTS 11,767,365 B2 * 9/2023 Sussman ................ A61K 31/40
424/133.1

FOREIGN PATENT DOCUMENTS

| CN | 102421801 A | 4/2012 |
| CN | 103562225 A | 2/2014 |
| JP | 2014520088 B2 | 8/2014 |
| WO | 2012/163805 A1 | 12/2012 |
| WO | 2017/143069 A1 | 8/2017 |
| WO | 2019/108900 A1 | 6/2019 |
| WO | 2010/104949 A2 | 9/2020 |

OTHER PUBLICATIONS

Shah et al., B-cell maturation antigen (BCMA) in multiple myeloma: rationale for targeting and current therapeutic approaches, Leukemia, 34:985-1005, 2020.*
Yu et al., BCMA-targeted immunotherapy for multiple myeloma, J. Hematol. Oncol. 13:125, 24 pages, 2020.*
Nezlin, R.S., Biochemistry of Antibodies, (Plenum PressLNY), Translation by M.C. Vale, 1970, p. 160).*
MacCallum et al., Antibody-antigen interactions: contact analysis and binding site topography, J. Mol. Biol. 262:732-745, 1996.*
Kunik et al., Structural consensus among antibodies defines the antigen binding site, PLoS Comput. Biol. 8(2):e1002388, doi: 10.1371/journal.pcbi.1002388, 17 pages, 2012.*
Chen et al., Enhancement and destruction of antibody function by somatic mutation: unequal occurrence is controlled by V gene combinatorial association, EMBO J. 14(12):2784-2794, 1995.*
Herold et al., Determinants of the assembly and function of antibody variable domains, Scientific Reports, 7:12276, DOI: 10.1038/s41598-017-12519-9, Sep. 2017.*
Kranz et al., Restricted reassociation of heavy and light chains from hapten-specific monoclonal antibodies, Proc. Natl. Acad. Sci., USA, 78(9):5807-5811, 1981.*
International Search Report mailed May 10, 2021, issued in International Publication No. PCT/CN2021/076319, 12 pages.
International Written Opinion mailed May 10, 2021, issued in International Publication No. PCT/CN2021/076319, 7 pages.
Bu, D-X., et al., "Pre-Clinical Validation of B Cell Maturation Antigen (BCMA) as a Target for T Cell Immunotherapy of Multiple Myeloma," Oncotarget 9(40):25764-25780, May 2018.
Buelow, B., et al., "TNB383B-0001: A Multicenter, Phase 1, Open-Label, Dose-Escalation Andexpansion Study of TNB383B, a Bispecific Antibodytargeting BCMA in Subjects with Relapsed or Refractorymultiple Myeloma," Blood 134(Suppl. 1):1874, Nov. 2019, 3 pages.
Costello, C.L., et al., "Phase 2 Study of the Response and Safety of P-Bcma-101 CAR-T Cells in Patients with Relapsed/Refractory (r/r) Multiple Myeloma (MM) (PRIME)," Blood 134(Suppl. 1):3184, Nov. 2019, 3 pages.

(Continued)

*Primary Examiner* — Claire Kaufman

(74) *Attorney, Agent, or Firm* — Christensen O'Connor Johnson Kindness PLLC

(57) ABSTRACT

Provided in the present invention are an anti-BCMA antibody, a pharmaceutical composition of same, and applications thereof. The anti-BCMA antibody of the present invention or an antigen binding fragment of same and the pharmaceutical composition thereof are applicable in treating B cell-related diseases.

6 Claims, 4 Drawing Sheets

Specification includes a Sequence Listing.

(56) References Cited

OTHER PUBLICATIONS

Panowski, S.H., et al., "Preclinical Efficacy and Safety Comparison of CD3 Bispecific and ADC Modalities Targeting BCMA for the Treatment of Multiple Myeloma," Molecular Cancer Therapeutics 18(11):2008-2020, Nov. 2019.

Raje, N.S., et al., "Safety, Clinical Activity, Pharmacokinetics, and Pharmacodynamics from a Phase I Study of PF-06863135, a B-Cell Maturation Antigen (BCMA)-CD3 Bispecific Antibody, in Patients with Relapsed/Refractory Multiple Myeloma (RRMM)," Blood 134(Suppl. 1):1869, Nov. 2019, 3 pages.

Wudhikarn, K., et al., "Monoclonal Antibodies in Multiple Myeloma: Current and Emerging Targets and Mechanisms of Action," Best Practice & Research Clinical Haematology 33(1):101143, Mar. 2020, 21 pages.

Extended European Search Report mailed Jun. 3, 2024, issued in related EP Application No. 21754265.3, filed Feb. 9, 2021, 13 pages.

Notice of Refusal mailed Jan. 15, 2025, issued in related JP Application No. 2022-549206, filed Sep. 17, 2020, 15 pages.

* cited by examiner

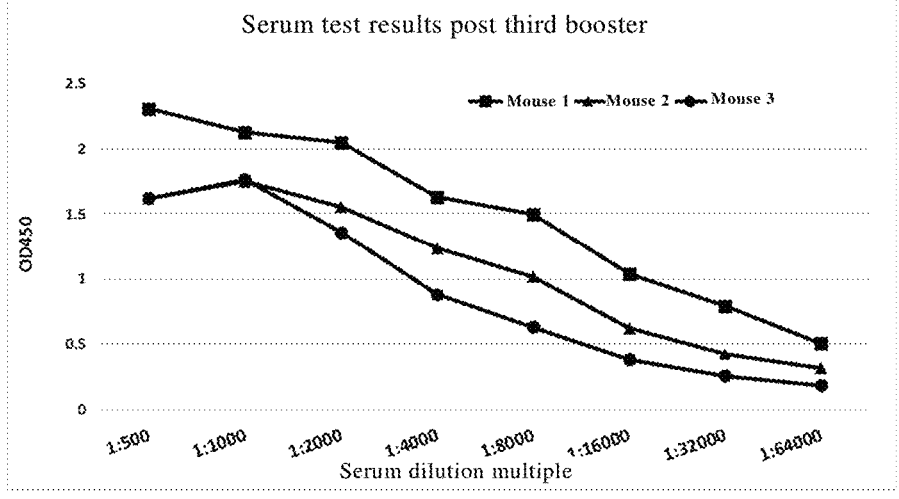
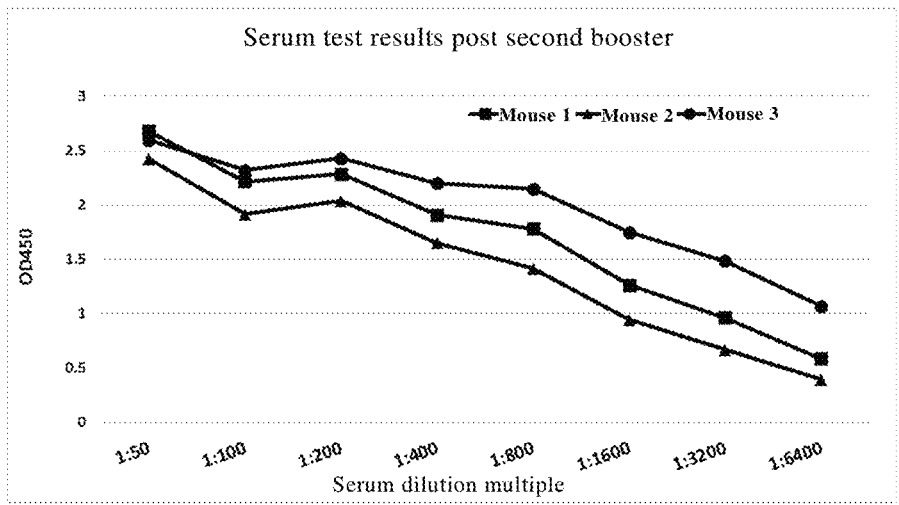
Fig. 1 (continue)

ANTI-BCMA ANTIBODY, PHARMACEUTICAL COMPOSITION OF SAME, AND APPLICATIONS THEREOF

STATEMENT REGARDING SEQUENCE LISTING

The Sequence Listing associated with this application is provided in text format and is hereby incorporated by reference into the specification. The name of the text file containing the sequence listing is 4259-P1USPNP_Seq_List_20221223_ST25. The text file is 48,107 bytes; was created on Dec. 23, 2022 and is being submitted via Patent Center with the filing of the specification.

TECHNICAL FIELD

This description relates to anti-BCMA antibodies, pharmaceutical composition thereof and use thereof.

BACKGROUND

B cell maturation antigen (BCMA), as a B cell surface molecule also known as CD269, consists of 184 amino acid residues, containing intracellular region of 80 amino acid residues and extracellular region sequence with only one carbohydrate recognition domain. BCMA is a type I transmembrane signaling protein lacking a signal peptide and a member of the tumor necrosis factor receptor family, which can bind to two types of ligands, B cell activating factor (BAFF) or a proliferation-inducing ligand (APRIL), respectively. In normal tissues, BCMA is expressed on the surface of mature B cells and plasma cells. The immune system of BCMA knockout mice behaves normally, with regular spleen structure and normal development of B lymphocytes. However, the number of plasma cells is significantly reduced, demonstrating that BCMA plays an important role in maintain the viability of plasma cells. Mechanistically, BCMA mainly includes the combination of BCMA and BAFF protein, promotes the expression of pro-survival genes, like Bcl-2, Mcl-1, and Bclw by interacting with BAFF, therefore maintaining the cell survival and growth. Likewise, this mechanism is employed by myeloma cells as well, contributing to the over-proliferation of myeloma cells. Previous studies suggest that BCMA is ubiquitously expressed in multiple myeloma cells of established cell lines and human patients. Based on previous reports, Kochenderfer et al. studied the expression pattern of BCMA in depth by combining Q-PCR, flow cytometry and immunohistochemical methods, and confirmed that BCMA is barely expressed in normal human tissues other than mature B cells and plasma cells, nor in CD34$^+$ hematopoietic cells.

SUMMARY OF DESCRIPTION

This description provides an anti-BCMA antibody or an antigen-binding fragment thereof, the anti-BCMA antibody comprises at least one CDR selected from the following sequences: SEQ II) NO: 1, SEQ II) NO: 2, SEQ ID NO: 3, SEQ ID NO: 4, SEQ ID NO: 5, SEQ ID NO: 6. SEQ LD NO: 7, SEQ ID NO: 8, and SEQ ID NO: 9.

In one or more embodiments, the anti-BCMA antibody comprises HCDR1 as set forth in SEQ ID NO:1, HCDR2 as set forth in SEQ ID NO:2, and HCDR3 as set forth in SEQ ID NO:3, 4 or 5, and/or comprises LCDR1 as set forth in SEQ ID NO: 6 or 7, LCDR2 as set forth in SEQ ID NO: 8 and LCDR3 as set forth in SEQ ID NO: 9.

In one or more embodiments, the anti-BCMA antibody comprises HCDR1 as set forth in any of SEQ ID NO: 12, 20, 28, 36, 44, 52, 60, 68, 76, 84, 92 or 100, HCDR2 as set forth in any of SEQ ID NO: 13, 21, 29, 37, 45, 53, 61, 69, 77, 85, 93 or 101, and HCDR3 as set forth in any of SEQ ID NO: 14, 22, 30, 38, 46, 54, 62, 70, 78, 86, 94 or 102, and/or comprises LCDR1 as set forth in any of SEQ ID NO: 15, 23, 31, 39, 47, 55, 63, 71, 79, 87, 95 or 103, LCDR2 as set forth in any of SEQ ID NO: 16, 24, 32, 40, 48, 56, 64, 72, 80, 88, 96 or 104, and LCDR3 as set forth in any of SEQ ID NO: 17, 25, 33, 41, 49, 57, 65, 73, 81, 89, 97 or 105.

In one or more embodiments of the present description, the anti-BCMA antibody comprises HCDR1, HCDR2 and HCDR3 as set forth in any group of the following Group A to L:

| Group | HCDR1 | HCDR2 | HCDR3 |
|---|---|---|---|
| A | 12 | 13 | 14 |
| B | 20 | 21 | 22 |
| C | 28 | 29 | 30 |
| D | 36 | 37 | 38 |
| E | 44 | 45 | 46 |
| F | 52 | 53 | 54 |
| G | 60 | 61 | 62 |
| H | 68 | 69 | 70 |
| I | 76 | 77 | 78 |
| J | 84 | 85 | 86 |
| K | 92 | 93 | 94 |
| L | 100 | 101 | 102 | and/or LCDR1, LCDR2 and LCDR3 as shown in any group of the following Group 1 to 12:

| Group | LCDR1 | LCDR2 | LCDR3 |
|---|---|---|---|
| 1 | 15 | 16 | 17 |
| 2 | 23 | 24 | 25 |
| 3 | 31 | 32 | 33 |
| 4 | 39 | 40 | 41 |
| 5 | 47 | 48 | 49 |
| 6 | 55 | 56 | 57 |
| 7 | 63 | 64 | 65 |
| 8 | 71 | 72 | 73 |
| 9 | 79 | 80 | 81 |
| 10 | 87 | 88 | 89 |
| 11 | 95 | 96 | 97 |
| 12 | 103 | 104 | 105 |

In one or more embodiments of the present description, the anti-BCMA antibody comprises HCDR and LCDR as shown in any group of the following Group a to 1:

| Group | HCDR1 | HCDR2 | HCDR3 | LCDR1 | LCDR2 | LCDR3 |
|---|---|---|---|---|---|---|
| a | 12 | 13 | 14 | 15 | 16 | 17 |
| b | 20 | 21 | 22 | 23 | 24 | 25 |
| c | 28 | 29 | 30 | 31 | 32 | 33 |
| d | 36 | 37 | 38 | 39 | 40 | 41 |
| e | 44 | 45 | 46 | 47 | 48 | 49 |
| f | 52 | 53 | 54 | 55 | 56 | 57 |
| g | 60 | 61 | 62 | 63 | 64 | 65 |
| h | 68 | 69 | 70 | 71 | 72 | 73 |
| i | 76 | 77 | 78 | 79 | 80 | 81 |
| j | 84 | 85 | 86 | 87 | 88 | 89 |
| k | 92 | 93 | 94 | 95 | 96 | 97 |
| l | 100 | 101 | 102 | 103 | 104 | 105 |

In one or more embodiments, the FR1 of the anti-BCMA antibody VH is selected from the FR1 of the antibody 7E11, 8H7, 11B10, 11G1, 15A7, 15H6, 18D10, 20A2 or 23C4, the FR2 is selected from the FR2 of the antibody 7E11, 8H7, 11B10, 11 G1, 15A7, 15H6, 18D10 or 20A2, the FR3 is selected from FR3 of the antibody 7E11, 8H7, 11B10, 11G1, 15A7, 18D10, 20A2, 23C4 or 31F5, FR4 is selected from the FDR4 of 7E11, 8H7, 11B10, 11G1, 15A7, 15H6, 20A2 or 31F5; and/or FR1 of VL is selected from FR1 of the antibody 7E11, 8H7, 11B10, 11G1, 15A7, 15H6, 18D10 or 20A2, FR2 is selected from FR2 of the antibody 7E11, 8H7, 15A7, 15H6, 20A2, 23C4 or 31F5, FR3 is selected from FR3 of the antibody 7E11, 8H7, 11B10, 11 G1, 15A7, 18D10, 20A2, 23C4, 27A7 or 31F5, FR4 is selected from FR4 of antibody 7E11, 11B10, 11G1, 15A7, or 18D10.

In one or more embodiments, the FR regions of VH and VL of the anti-BCMA antibody are selected from the FR regions of VH and VL of any one of antibodies 7E11, 8H7, 11B10, 11G1, 15A7, 15H6, 18D10, 20A2, 20A9, 23C4, 27A7, and 31F5.

In one or more embodiments, the amino acid sequence of the VH of the anti-BCMA antibody is as shown in any one of SEQ ID NO: 10, 18, 26, 34, 42, 50, 58, 66, 74, 82, 90, and 98, and/or the amino acid sequence of the VL is as shown in any of SEQ ID NO: 11, 19, 27, 35, 43, 51, 59, 67, 75, 83, 91 and 99.

In one or more embodiments, the amino acid sequence of the VH of the anti-BCMA antibody is shown as SEQ ID NO: 10, the amino acid sequence of the VL is shown as SEQ ID NO: 11; or the amino acid sequence of the VH is shown as SEQ ID NO: 18, the amino acid sequence of the VL is shown as SEQ ID NO: 19; the amino acid sequence of the VH is shown as SEQ ID NO: 26, the amino acid sequence of the VL is shown as SEQ ID NO: 27; the amino acid sequence of the VH is shown as SEQ ID NO: 34, the amino acid sequence of the VL is shown as SEQ ID NO: 35; the amino acid sequence of the VH is shown as SEQ ID NO: 42, the amino acid sequence of the VL is shown as SEQ ID NO: 43; the amino acid sequence of the VH is shown as SEQ ID NO: 50, the amino acid sequence of the VL is shown as SEQ ID NO: 51; the amino acid sequence of the VH is shown as SEQ ID NO: 58, the amino acid sequence of the VL is shown as SEQ ID NO: 59; the amino acid sequence of the VH is shown as SEQ ID NO: 66, the amino acid sequence of the VL is shown as SEQ ID NO: 67; the amino acid sequence of the VH is shown as SEQ ID NO: 74, the amino acid sequence of the VL is shown as SEQ ID NO: 75; the amino acid sequence of the VH is shown as SEQ ID NO: 82, the amino acid sequence of the VL is shown as SEQ ID NO: 83; the amino acid sequence of the VH is shown as SEQ ID NO: 90, the amino acid sequence of the VL is shown as SEQ ID NO: 91; the amino acid sequence of the VH is shown as SEQ ID NO: 98, the amino acid sequence of the VL as shown in SEQ ID NO: 99.

In one or more embodiments, the heavy chain constant region sequence of the BCMA antibody according to any of the embodiments of the description is set forth in SEQ ID NO: 106, and/or the light chain constant region sequence is set forth in SEQ ID NO: 107.

In one or more embodiments, the anti-BCMA antibody of any of the embodiments of the description is a chimeric antibody or a complete human antibody; preferably a complete human antibody.

This description also provides a pharmaceutical composition comprising the anti-BCMA antibody or antigen-binding fragment thereof according to any embodiment of this description, and a pharmaceutically acceptable excipient or carrier.

This description also provides a nucleic acid molecule selected from: (1) a polynucleotide sequence encoding the anti-BCMA antibody or an antigen-binding fragment thereof according to any embodiment of this description; (2) the polynucleotide of (1) the complement of the sequence.

The present description also provides the use of the anti-BCMA antibody or its antigen-binding fragment according to any embodiment of the present description in the manufacture of a medicament for the treatment of B cell-related diseases; preferably, the B cell-related diseases are B cell-related tumors or autoimmune diseases.

This description also provides a method of treating or preventing B cell-related diseases, the method comprising administering to a patient in need thereof a therapeutically effective amount of the anti-BCMA antibody or antigen-binding fragment thereof according to any embodiment of this description, or a pharmaceutical composition containing the anti-BCMA antibody or antigen-binding fragment thereof of any embodiment of this description. Preferably, the B-cell-related disease is a B-cell-related tumor or an autoimmune disease.

DETAILED DESCRIPTION

Figure 1:
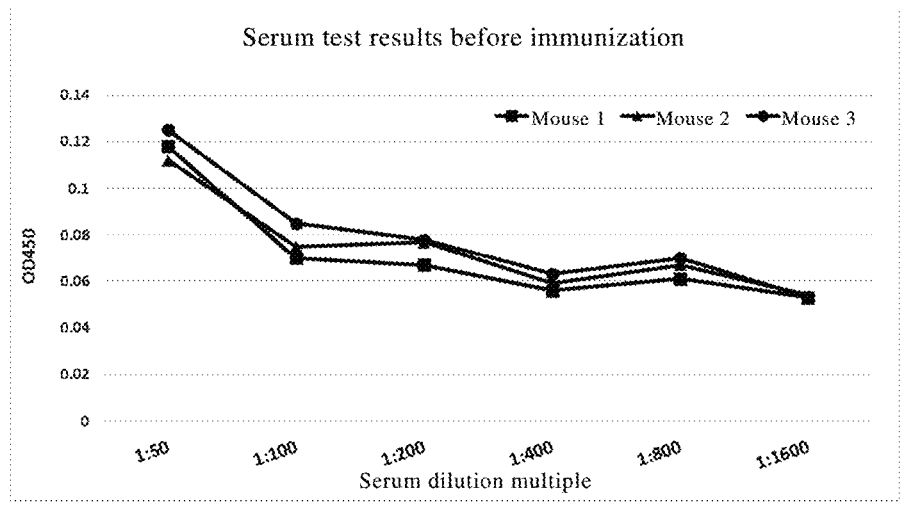
FIG. 1 shows the results of human BCMA-specific enzyme-linked immunosorbent assay detection in the serum of immunized animals in Example 2.
Figure 1:
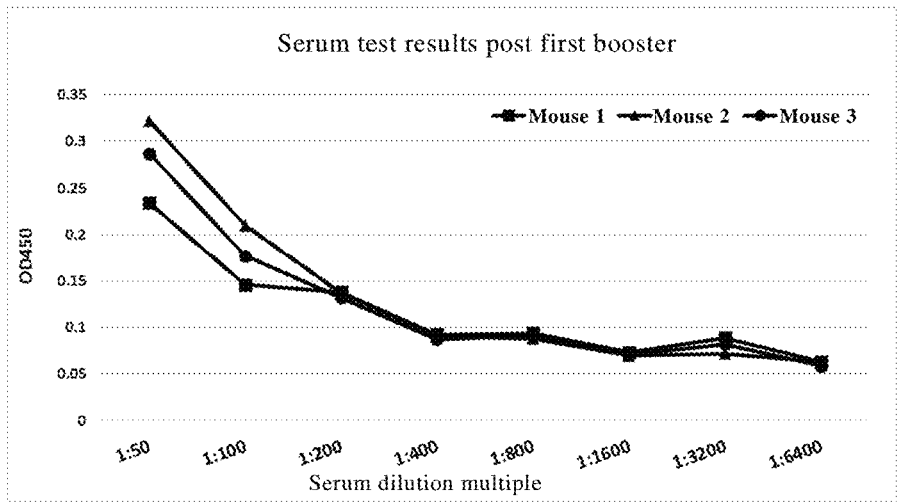

The practice of the present description will employ, unless otherwise indicated, conventional techniques of molecular biology (including recombinant techniques), microbiology, cell biology, biochemistry, and immunology, which are within the skill of the art. Such techniques are explained fully in the literature, such as Molecular Cloning: A Laboratory Manual, second edition (Sambrook et al., 1989), Oligonucleotide Synthesis (MJ. Gait, ed., 1984), Animal Cell Culture (RJ. Freshney, ed., 1987), Methods in Enzymology (Academic Press, Inc.), Current Protocols in Molecular Biology (F. M. Ausubel et al., eds 1987, and periodic updates), PCR: The Polymerase Chain Reaction, (Mullis et al., ed., 1994), A Practical Guide to Molecular Cloning (Perbal Bernard V., 1988), and Phage Display: A Laboratory Manual (Barbas et al., 2001).

BCMA

As used herein, "BCMA" refers to a cell surface receptor or receptor complex comprising BCMA that binds BAFF and/or APRIL. The NCBI accession number for the amino acid sequence of human BCMA (huBCMA) is Q02223 (GI: 313104029). BCMA proteins can also include variants and fragments. The fragments include an extracellular domain that do not have all or part of the transmembrane region, and/or fragments of the intracellular domain and the extracellular domain. Soluble forms of huBCMA include the extracellular domain or fragments of the extracellular domain that retain the ability to bind BAFF and/or APRIL. "BCMA" also includes post-translational modifications of the BCMA amino acid sequence. Post-translational modifications include, but are not limited to, N- and O-linked glycosylation.

Normal tissue expression of BCMA is highly restricted to the B cell lineage, predominantly in secondary follicle/embryonic centers of tonsil/lymph nodes, on plasmablasts, and on differentiated plasma cells. BCMA is expressed in malignant plasma cells at relatively higher levels than observed in normal plasma cells, especially highly expressed in multiple myeloma, smoldering myeloma and monoclonal gammopathy of undetermined significance (MGUS) plasma cells. BCMA is a favorable target for the treatment of BCMA-expressing B-cell-associated malignancies, as its expression is highly restricted to normal and malignant plasma cells and should therefore have minimal off-target toxicity to other tissues.

Anti-BCMA Antibody

This description provides antibodies that specifically bind BCMA.

The term "antibody" includes monoclonal antibodies (including full length antibodies which have an immunoglobulin Fc region), antibody compositions with polyepitopic specificity, multispecific antibodies (e.g., bispecific antibodies), diabodies, and single-chain molecules, as well as antibody fragments, e.g., Fab, F(ab')2, and Fv). The term "immunoglobulin" (Ig) is used interchangeably with "antibody" herein.

The basic four-chain antibody unit is a heterotetrameric glycoprotein composed of two identical light (L) chains and two identical heavy (H) chains. An IgM antibody consists of five basic heterotetramer units and an additional polypeptide called J chain, containing 10 antigen binding sites. While IgA antibodies comprise two to five basic four-chain units which can polymerize to form polyvalent assemblages in combination with the J chain. In the case of IgGs, the four-chain unit is generally about 150.000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has a variable domain (VH) at the N-terminus, followed by three constant domains (CH) for each of the $\alpha$ and $\gamma$ chains and four CH domains for $\mu$ and $\epsilon$ isotypes. Each L chain has a variable domain (VL) at the N-terminus, followed by a constant domain at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see e.g., Basic and Clinical Immunology, 8th Edition, Daniel P. Sties, Abba I. Terr and Tristram G. Parsolw (eds), Appleton & Lange, Norwalk, CT, 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated $\alpha$, $\delta$, $\epsilon$, $\gamma$ and $\mu$, respectively. The $\gamma$ and $\alpha$ classes are further divided into subclasses on the basis of relatively minor differences in the CH sequence and function, e.g., humans express the following subclasses: IgG1, IgG2A, IgG2B, IgG3, IgG4, IgA1 and IgA2.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its specific antigen. However, the variability is not evenly distributed in the secondary sequence (amino acid sequence) across the variable domains. Instead, it is mainly in three segments called hypervariable regions (HVRs) existing in both the VH and VL, i.e., LCDR1, LCDR2 and LCDR3 in VL and HCDR1, HCDR2 and HCDR3 in VH. The highly conserved portions of variable domains are called the framework regions (FR). The variable domains of native heavy and light chains, each comprise four FR regions (FR1, FR2, FR3 and FR4), largely adopting a beta-sheet configuration, connected by three HVRs, which form connecting loops, and in some cases forming part of, the beta-sheet structure. The HVRs in each chain are held together in close proximity by the FR regions and, with the HVRs from the other chain, contribute to the formation of the antigen binding site of antibodies (see Kabat et al, Sequences of Immunological Interest, Fifth Edition, National Institute of Health, Bethesda, MD (1991)). Typically, the structure of the light chain variable region is FR1-LCDR1-FR2-LCDR2-FR3-LCDR3-FR4, and the structure of the heavy chain variable region is FR1-HCDR1-FR2-HCDR2-FR3-HCDR3-FR4. The constant domains are not involved directly in the binding of antibody to an antigen, but exhibit various effector functions, such as engaging the antibody in antibody-dependent cellular toxicity.

The term "monoclonal antibody" as used herein refers to an antibody obtained from a population of substantially homogeneous antibodies, i.e., the individual antibodies comprising the population are identical except for potential naturally occurring mutations and/or post-translation modifications (e.g., isomerization, amination) that may be present minorly. Monoclonal antibodies are highly specific, being directed against a unique epitope. In contrast to polyclonal antibodies which typically contain different antibodies directed against various epitopes, each monoclonal antibody is directed against a unique epitope on the antigen. In addition to their specificity, the monoclonal antibodies are advantageous in that they are produced by the hybridoma culture, devoid of the contamination by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present description may be made by a variety of techniques, including, for example, the hybridoma (e.g., Kohler and Milstein., Nature, 256:495-97 (1975); Hongo et al, Hybridoma, 14 (3): 253-260 (1995), Harlow et al. Antibodies: A Laboratory Manual, (Cold Spring Harbor Laboratory Press, 2nd ed. 1988); Hammerling et al, in: Monoclonal Antibodies and T-Cell Hybridomas 563-681 (Elsevier, N. Y., 1981)), DNA recombination (see, e.g., U.S. Pat. No. 4,816,567), phage-display (see, e.g., Clackson et al. Nature, 352: 624-628 (1991); Marks et al, J. Mol Biol. 222: 581-597 (1992); Sidhu et al, J. Mol Biol. 338(2): 299-310 (2004); Lee et al, J. Mol Biol. 340(5):

1073-1093 (2004); Fellouse, Proc. Natl. Acad. ScL USA 101(34): 12467-12472 (2004); and Lee et al, J. Immunol. Methods 284(1-2): 119-132 (2004), and technologies for producing human or humanlike antibodies in animals that have parts or all of the human immunoglobulin loci or genes encoding human immunoglobulin sequences (see, e.g., WO 1998/24893; WO 1996/34096: WO 1996/33735; WO 1991/ 10741; Jakobovits et al, Proc. Natl. Acad. ScL USA 90: 2551 (1993); Jakobovits et al, Nature 362: 255-258 (1993); Bruggemann et al, Year in Immunol. 7:33 (1993); U.S. Pat. Nos. 5,545,807; 5,545,806; 5,569,825; 5,625,126; 5,633, 425; and 5,661,016; Marks et al, Bio/Technology 10: 779-783 (1992); Lonberg et al, Nature 368: 856-859 (1994); Morrison, Nature 368: 812-813 (1994); Fishwild et al, Nature Biotechnol 14: 845-851 (1996); Neuberger, Nature Biotechnol. 14: 826 (1996); and Lonberg and Huszar, Intern. Rev. Immunol. 13: 65-93 (1995).

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Antibody fragments are preferably antigen-binding fragments of antibodies. Examples of antibody fragments include Fab, Fab', F(ab')2 and Fv fragments; diabodies; linear antibodies (see U.S. Pat. No. 5,641, 870, Example 2; Zapata et al. Protein Eng., 8(10): 1057-1062, 1995); single-chain antibody molecules; scFv-Fc fragments; multispecific antibodies formed from antibody fragments; and any fragment that should be able to increase half-life by chemical modification or by incorporation into liposomes. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having different antigen-binding activity and is still capable of cross-linking antigen. Fab' fragments differ from Fab fragments by having a few additional residues at the carboxy terminus of the CH1 domain including one or more cysteines from the antibody hinge region. F(ab')2 antibody fragments originally were produced as pairs of Fab' fragments which have hinge cysteines between them. Other chemical couplings of antibody fragments are also known. The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) can recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of the sFv, refer to/see The Pharmacology of Monoclonal Antibodies, vol. 113. Rosenburg and Moore eds., Springer-Verlag, New York, pp. 269-315 (1994).

"Chemical modification" of the fragments includes the addition of poly(alkylene) glycols such as polyethylene glycol ("PEGylated, PEGylated"), including PEGylated fragments of Fv, scFv, Fab, F(ab')2 and Fab', namely Fv-PEG, scFv-PEG, Fab-PEG, F(ab')2-PEG and Fab'-PEG. Such fragments have EGFR binding activity.

Preferably, the antibody fragment, especially the antigen-binding fragment, consists of or comprises a partial sequence of the variable heavy or light chain of the antibody from which it is derived, said partial sequence being sufficient to retain the same binding specificity and sufficient affinity as the antibody from which it is derived, for BCMA, the affinity of the antibody fragment are preferably equal to at least 1/100, and more preferably equal to at least 1/10, of the affinity of the antibody from which it is derived. Such antibody fragments will contain a minimum of 5 amino acids, preferably 10, 15, 25, 50 and 100 contiguous amino acids of the antibody sequence from which they are derived.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567: Morrison et al, Proc. Natl. Acad. ScL USA, 81:6851-6855 (1984)).

"Humanized" forms of non-human (e.g., murine) antibodies are chimeric antibodies that contain minimal sequence derived from non-human immunoglobulin. Thus, a "humanized antibody" generally refers to a non-human antibody in which the variable domain framework regions are exchanged with sequences found in human antibodies. Typically in a humanized antibody, the entire antibody (except the CDRs) is encoded by a polynucleotide of human origin or is identical to such antibody (except for the CDRs). CDRs (some or all of which are encoded by nucleic acids derived from non-human organisms) are grafted into the βsheet backbone of the variable regions of human antibodies to generate antibodies, the specificity of which is determined by the grafted CDRs. The production of such antibodies is described, for example, in WO92/11018; Jones, 1986, Nature, 321:522-525; Verhoeyen et al., 1988, Science, 239: 1534-1536. Humanized antibodies can also be generated using mice with genetically engineered immune systems (see Roque et al., 2004, Biotechnol. Prog., 20:639-654).

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Such techniques are described in Hoogenboom and Winter, J. Molecular Biology, 227:381 (1991); Marks et al., J. Molecular Biology, 222:581 (1991). Available methods for preparing human monoclonal antibodies are described in Cole et al., Monoclonal Antibodies and Cancer Therapy, Alan R. Liss, p. 77 (1985); Boerner et al., J. Immunol., 147(1): 86-95 (1991)). See also van Dijk and van de Winkel, Modern Pharmacy Reviews, 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al, Proc. Natl. Acad. Sci. USA, 103:3557-3562 (2006) regarding human antibodies generated via a human B-cell hybridoma technology.

BCMA antibodies of this description may also be minibodies. Minibodies are minimal antibody-like proteins comprising scFv linked to the CH3 domain (Hu et al., 1996, Cancer Res., 56:3055-3061). Anti-BCMA antibodies of the description may also be domain antibodies, see eg. U.S. Pat. No. 6,248,516. Domain antibodies (dAbs) are functional binding domains of antibodies, corresponding to the variable regions of the heavy (VH) or light (VL) chains of human antibody dABs, with a molecular weight of about 13 kDa or a size less than $\frac{1}{10}$ of an intact antibody. dABs are well expressed in a variety of hosts including bacterial, yeast and mammalian cell systems. Additionally, the dAbs are highly stable and remain active even after being subjected to harsh conditions, such as freeze-drying or thermal denaturation. See references eg. U.S. Pat. No. 6,291,158: U.S. Pat. No. 6,582,915: U.S. Pat. Nos. 6,593,081; 6,172,197; US 2004/0110941; EP 0368684; U.S. Pat. No. 6,696,245; WO04/058821: WO04/003019; and WO03/002609.

HCDR1 of the anti-BCMA antibody of the present description may contain $GX_1TX_2X_3X_4X_5X_6$ (SEQ ID NO: 1), wherein $X_1$ is F or Y, $X_2$ is F or S, $X_3$ is S, D, T, N or A, $X_4$ is Y, D, S or A, $X_5$ is Y, C or H, $X_6$ is D, A or Y. In some embodiments, $X_1$ is F, $X_2$ is F, $X_3$ is A or D, $X_4$ is D, $X_5$ is Y, C or H, and $X_6$ is A. In some embodiments, $X_1$ is Y, $X_2$ is F, $X_3$ is T, $X_4$ is S or A, $X_5$ is Y, and $X_6$ is A or Y. Exemplary amino acid sequences of HCDR1 are set forth in any of SEQ ID NO: 12, 20, 28, 36, 44, 52, 60, 68, 76, 84, 92, or 100.

HCDR2 of the anti-BCMA antibody of this description may contain $IX_1X_2X_3X_4X_5X_6X_7$ (SEQ ID NO: 2), wherein $X_1$ is S, N or Y, $X_2$ is W, T, A, or P, $X_3$ is N or G, $X_4$ is S or N, $X_5$ is D, G or V, $X_6$ is T, N, S, D or H, $X_7$ is I, M or T. In some embodiments, $X_1$ is S, $X_2$ is W, $X_3$ is N, $X_4$ is S, $X_5$ is D or V, $X_6$ is T, N, H or S, $X_7$ is I; preferably, in these embodiments, $X_8$ is D, $X_6$ is H or N. In some embodiments, $X_1$ is N, $X_2$ is T or A, $X_3$ is G, $X_4$ is N, $X_5$ is G, $X_6$ is N, $X_7$ is T or I. Exemplary amino acid sequences of HCDR2 are set forth in any of SEQ ID NO: 13, 21, 29, 37, 45, 53, 61, 69, 77, 85, 93, or 101.

HCDR3 of the anti-BCMA antibody of the present description may contain $ARGGX_1X_2X_3X_4X_5X_6X_7YYX_8YYMDV$ (SEQ ID NO:3), wherein $X_1$ is S or R, $X_2$ is I or L, $X_3$ is T or E, $X_4$ is G or L, $X_5$ is N or D, $X_6$ is I or V, $X_7$ is F or Y, $X_8$ is Y or F; in some embodiments, $X_1$ is R, $X_2$ is L, $X_3$ is E, $X_4$ is L, $X_5$ is D, $X_6$ is I or V, $X_7$ is Y, $X_8$ is F. In some embodiments, HCDR 3 of an anti-BCMA antibody of the description may contain $X_1X_2X_3X_4X_5X_6X_7FDY$ (SEQ ID NO: 4), wherein $X_1$ is A or T, $X_2$ is K, R or T, $X_3$ is V or IQ, $X_4$ is S, V or A, $X_5$ is G, S or A, $X_6$ is A or S, $X_7$ is V, S, Y or T. In some embodiments, the anti-BCMA antibody comprises $AKDIFSPTGDX_1Y$ (SEQ ID NO: 5), wherein, $X_1$ is G or D. Exemplary amino acid sequences of HCDR3 are set forth in any of SEQ ID NO: 14, 22, 30, 38, 46, 54, 62, 70, 78, 86, 94, or 102.

LCDR1 of the anti-BCMA antibody of the present description may contain $QX_1IX_2X_3X_4$ (SEQ ID NO: 6), wherein $X_1$ is S or D, $X_2$ is H, I, S, or R, $X_3$ is S, N, or T, $X_4$ is Y, F, or N. In some embodiments, $X_1$ is S or D, $X_2$ is I, $X_3$ is S, $X_4$ is S or T, $X_5$ is Y. In some embodiments, LCDR1 of an anti-BCMA antibody of the description may contain $QSX_1X_2X_3X_4X_5X_6X_7X_8Y$ (SEQ ID NO: 7), wherein $X_1$ is L, V, or F, $X_2$ is L or V, $X_3$ is H, Y, or S, $X_4$ is S or SS, $X_5$ is N, Q, or D, $X_6$ is G or N, $X_7$ is Y, K, or N, $X_8$ is N or T. In some embodiments, $X_1$ is L or V, $X_2$ is L, $X_3$ is H, $X_4$ is S or SS, $X_5$ is N, Q, or D, $X_6$ is G or N, $X_7$ is K, $X_8$ is N. Exemplary amino acid sequences of LCDR1 are set forth in any of SEQ ID NO: 15, 23, 31, 39, 47, 55, 63, 71, 79, 87, 95, or 103.

LCDR2 of the anti-BCMA antibody of this description may contain $X_1X_2S$ (SEQ ID NO: 8), wherein $X_1$ is L, S, W, G, A, or K, $X_2$ is G, A, or L. In some embodiments, $X_1$ is S, W, G, or A, $X_2$ is A. Exemplary amino acid sequences of LCDR2 are set forth in any of SEQ ID NO: 16, 24, 32, 40, 48, 56, 64, 72, 80, 88, 96, or 104.

LCDR3 of the anti-BCMA antibody of this description may contain $X_1X_2X_3X_4X_5X_6X_7X_8X_9$ (SEQ ID NO: 9), wherein $X_1$ is M, Q, or L, $X_2$ is Q, G, or H, $X_3$ is A, S, Y, R, or H, $X_4$ is L, F, Y, T or N, $X_8$ is Q, S, R, I, or H, $X_6$ is T, I, P, V, W, or Y, $X_7$ is P or L, $X_8$ is Y, F, L, or P, $X_9$ is T or I. In some embodiments, $X_1$ is Q, $X_2$ is Q, $X_3$ is S or Y, $X_4$ is F, Y or S, $X_5$ is S or R, $X_6$ is I or P, $X_7$ is P or L, $X_8$ is Y, L, or F, $X_9$ is T. Exemplary amino acid sequences of LCDR3 are set forth in any of SEQ ID NO: 17, 25, 33, 41, 49, 57, 65, 73, 81, 89, 97, or 105.

In some embodiments, the anti-BCMA antibody of this description comprises HCDR1 as set forth in SEQ ID NO:1, HCDR2 as set forth in SEQ ID NO:2, and HCDR3 as set forth in SEQ ID NO:3, 4 or 5, and/or LCDR1 as set forth in SEQ ID NO: 6 or 7, LCDR2 as set forth in SEQ ID NO: 8 and LCDR3 as set forth in SEQ ID NO: 9. Preferably, the anti-BCMA antibody of this description comprises HCDR1 as set forth in any of SEQ ID NO: 12, 20, 28, 36, 44, 52, 60, 68, 76, 84, 92 or 100, HCDR2 as set forth in any of SEQ ID NO: 13, 21, 29, 37, 45, 53, 61, 69, 77, 85, 93 or 101, and HCDR3 as set forth in any of SEQ ID NO: 14, 22, 30, 38, 46, 54, 62, 70, 78, 86, 94 or 102, and/or LCDR1 as set forth in any of SEQ ID NO: 15, 23, 31, 39, 47, 55, 63, 71, 79, 87, 95 or 103, LCDR2 as set forth in any of SEQ ID NO: 16, 24, 32, 40, 48, 56, 64, 72, 80, 88, 96 or 104, and LCDR3 as set forth in any of SEQ ID NO: 17, 25, 33, 41, 49, 57, 65, 73, 81, 89, 97 or 105.

Further preferably, the anti-BCMA antibody of this description contains HCDR1, HCDR2 and HCDR3 shown in an group of the following Groups A to L:

| Group | HCDR1 | HCDR2 | HCDR3 |
|-------|-------|-------|-------|
| A | 12 | 13 | 14 |
| B | 20 | 21 | 22 |
| C | 28 | 29 | 30 |

-continued

| Group | HCDR1 | HCDR2 | HCDR3 |
|---|---|---|---|
| D | 36 | 37 | 38 |
| E | 44 | 45 | 46 |
| F | 52 | 53 | 54 |
| G | 60 | 61 | 62 |
| H | 68 | 69 | 70 |
| I | 76 | 77 | 78 |
| J | 84 | 85 | 86 |
| K | 92 | 93 | 94 |
| L | 100 | 101 | 102 | and/or LCDR1, LCDR2 and LCDR3 as shown in any group of the following Group 1 to 12:

| Group | LCDR1 | LCDR2 | LCDR3 |
|---|---|---|---|
| 1 | 15 | 16 | 17 |
| 2 | 23 | 24 | 25 |
| 3 | 31 | 32 | 33 |
| 4 | 39 | 40 | 41 |
| 5 | 47 | 48 | 49 |
| 6 | 55 | 56 | 57 |
| 7 | 63 | 64 | 65 |
| 8 | 71 | 72 | 73 |
| 9 | 79 | 80 | 81 |
| 10 | 87 | 88 | 89 |
| 11 | 95 | 96 | 97 |
| 12 | 103 | 104 | 105 |

Further preferably, the anti-BCMA antibody of this description contains HCDR and LCDR shown in any group of the following Group a to 1:

| Group | HCDR1 | HCDR2 | HCDR3 | LCDR1 | LCDR2 | LCDR3 |
|---|---|---|---|---|---|---|
| a | 12 | 13 | 14 | 15 | 16 | 17 |
| b | 20 | 21 | 22 | 23 | 24 | 25 |
| c | 28 | 29 | 30 | 31 | 32 | 33 |
| d | 36 | 37 | 38 | 39 | 40 | 41 |
| e | 44 | 45 | 46 | 47 | 48 | 49 |
| f | 52 | 53 | 54 | 55 | 56 | 57 |
| g | 60 | 61 | 62 | 63 | 64 | 65 |
| h | 68 | 69 | 70 | 71 | 72 | 73 |
| i | 76 | 77 | 78 | 79 | 80 | 81 |
| j | 84 | 85 | 86 | 87 | 88 | 89 |
| k | 92 | 93 | 94 | 95 | 96 | 97 |
| l | 100 | 101 | 102 | 103 | 104 | 105 |

The FR1 of the anti-BCMA antibody VH of this description can be selected from the FR1 of the antibody 7E11, 8H7, 11B10, 11G1, 15A7, 15H6, 18D10, 20A2 or 23C4, the FR2 is selected from the FR2 of the antibody 7E11, 8H7, 11B10, 11G1, 15A7, 15H6, 18D10 or 20A2, the FR3 is selected from FR3 of the antibody 7E11, 8H7, 11B10, 11G1, 15A7, 18D10, 20A2, 23C4 or 31F5, FR4 is selected from the FR4 of 7E11, 8H7, 11B10, 11G1, 15A7, 15H6, 20A2 or 31F5; and/or FR1 of VL is selected from FR1 of the antibody 7E11, 8H7, 11B10, 11G1, 15A7, 15H6, 18D10 or 20A2, FR2 is selected from FR2 of the antibody 7E11, 8H7, 15A7, 15H6, 20A2, 23C4 or 31F5, FR3 is selected from FR3 of the antibody 7E11, 8H7, 11B10, 11G1, 15A7, 18D10, 20A2, 23C4, 27A7 or 31F5, FR4 is selected from FR4 of antibody 7E11, 11B10, 11G1, 15A7, or 18D10.

In preferable embodiments, the FR regions of VH and VL of the anti-BCMA antibody in this description are selected from the FR regions of VH and VL of any of antibodies 7E11, 8H7, 11B10, 11G1, 15A7, 15H6, 18D10, 20A2, 20A9, 23C4, 27A7, and 31F5. Further preferably, HCDRs of these antibodies are selected from any group of the above Group A to L, and the LCDRs are selected from any group of the above Group 1 to 12; more preferably, the CDRs of such antibodies are selected from the aforementioned any group of the above Group a to Group 1.

In some embodiments, the amino acid sequence of the VH of the anti-BCMA antibody in this description is as shown in any one of SEQ ID NO: 10, 18, 26, 34, 42, 50, 58, 66, 74, 82, 90, and 98, and/or the amino acid sequence of the VL is as shown in any of SEQ ID NO: 11, 19, 27, 35, 43, 51, 59, 67, 75, 83, 91 and 99. Preferably, the amino acid sequence of the VH of the anti-BCMA antibody in this description is shown in SEQ ID NO: 10, the amino acid sequence of the VL is shown in SEQ ID NO: 11; or the amino acid sequence of the VH is shown in SEQ ID NO: 18, the amino acid sequence of the VL is shown in SEQ ID NO: 19; the amino acid sequence of the VH is shown in SEQ ID NO: 26, the amino acid sequence of the VL is shown in SEQ ID NO: 27; the amino acid sequence of the VH is shown in SEQ ID NO: 34, the amino acid sequence of the VL is shown in SEQ ID NO: 35; the amino acid sequence of the VH is shown in SEQ ID NO: 42, the amino acid sequence of the VL is shown in SEQ ID NO: 43; the amino acid sequence of the VH is shown in SEQ ID NO: 50, the amino acid sequence of the VL is shown in SEQ ID NO: 51; the amino acid sequence of the VH is shown in SEQ ID NO: 58, the amino acid sequence of the VL is shown in SEQ ID NO: 59; the amino acid sequence of the VH is shown in SEQ ID NO: 66, the amino acid sequence of the VL is shown in SEQ ID NO: 67; the amino acid sequence of the VH is shown in SEQ ID NO: 74, the amino acid sequence of the VL is shown in SEQ ID NO: 75; the amino acid sequence of the VH is shown in SEQ ID NO: 82, the amino acid sequence of the VL is shown in SEQ ID NO: 83; the amino acid sequence of the VH is shown in SEQ ID NO: 90, the amino acid sequence of the VL is shown in SEQ ID NO: 91; the amino acid sequence of the VH is shown in SEQ ID NO: 98, the amino acid sequence of the VL is shown in SEQ ID NO: 99.

In some embodiments, the amino acid sequence of the heavy chain constant region sequence of the BCMA antibody in the description is set forth in SEQ ID NO: 106, and/or the light chain constant region sequence is set forth in SEQ ID NO: 107.

The antibody of the description can be a chimeric antibody, a humanized antibody or a complete human antibody; preferably a complete human antibody. It should be understood that the antibodies provided in the embodiments of the present description are complete human antibodies.

Under the premise that the activity of the antibody is not substantially affected, the sequences of the present description can be substituted, added and/or deleted by one or more (eg. 1, 2, 3, 4, 5, 6, 7, 8, 9 or 10 or more) amino acids by those skilled in the art to obtain variants of the antibody or functional fragment sequence thereof. All of them are included in the scope of protection of this description. For example, amino acids with similar properties are substituted in the FR and/or CDR regions of the variable region. Substitutions are preferably conservative substitutions; amino acid residues that can be conservatively substituted are well known in the art. In some embodiments, the variant of this description may be at least 95%, 96%, 97%, 98% or 99% identical to the sequence from which it was derived. Sequence identity according to the present description can be measured using sequence analysis software. For example, the computer programs BLAST using default parameters, especially BLASTP or TBLASTN.

The anti-BCMA antibodies of the description can be modified to affect function. The present description includes anti-BCMA antibodies with modified glycosylation sites. Modifications can be made to remove undesired glycosylation sites, or remove fucose moieties from oligosaccharide chains to enhance antibody-dependent cytotoxicity (ADCC) function, or add galactosylation to alter complement dependent cytotoxicity (CIXC).

Anti-BCMA antibodies of the description can typically have affinity constants (KD) of about $10^{-9}$ to about $10^{-13}$ M.

The anti-BCMA antibodies of this description can be prepared by conventional methods in the art, such as hybridoma technology well known in the art. Alternatively, the anti-BCMA antibodies of this description can be expressed in cell lines other than hybridoma cell lines. Suitable mammalian host cells can be transformed with sequences encoding the antibodies of the description. Transformation can be carried out by any known method including, for example, packaging the polynucleotide in a virus (or viral vector) and transducing the host cell with the virus (or vector). The transformation procedure used will depend in the host to be transformed. Methods for introducing heterologous polynucleotides into mammalian cells are well known in the art and include dextran-mediated transfection, calcium phosphate precipitation, polybrene-mediated transfection, protoplast fusion, electroporation, encapsulation of polynucleotides in liposomes and direct microinjection of DNA into the nucleus. Mammalian cell lines that can be used as hosts for expression are well known in the art and include, but are not limited to, various immortalized cell lines available from the American Type Culture Collection (ATCC), including but not limited to Chinese Hamster Ovary (CHO) cells, HeLa cells, baby hamster kidney (BHK) cells, monkey kidney cells (COS), human hepatocellular carcinoma cells (e.g., HepG2), etc. Particularly preferred cell lines are selected by determining which cell lines have high expression levels and produce antibodies with substantial BCMA binding properties.

Polynucleotide Sequences Encoding Anti-BCMA Antibodies

The present description provides nucleic acid molecules comprising polynucleotide sequences encoding the anti-BCMA antibodies of this description. Provided herein are polynucleotide sequences encoding heavy chain variable regions, light chain variable regions, heavy chains, light chains, and each CDR.

DNA and RNA in single- and double-stranded forms, as well as corresponding complementary sequences. DNA includes, for example, cDNA, genomic DNA, chemically synthesized DNA, PCR amplified DNA, and combinations thereof. Nucleic acid molecules of the present description include full-length genes or cDNA molecules and combinations of fragments thereof. Nucleic acids of this description are preferably derived from human sources, but the description also includes nucleic acids derived from non-humans.

In this description, an isolated nucleic acid molecule refers to a nucleic acid molecule in the form of individual fragments or as a component of a larger nucleic acid construct. In a preferred embodiment, the nucleic acid is substantially free of contaminating endogenous material. Nucleic acid molecules are preferably derived from DNA or RNA that has been isolated at least once in substantially pure form and in an amount or concentration that enables identification, manipulation and recovery of its constituent nucleotide sequences by standard biochemical methods. The sequences are preferably provided and/or constructed as open reading frames uninterrupted by internal untranslated sequences or introns (typically found in eukaryotic genes). Sequences of untranslated DNA may be present 5' or 3' to the open reading frame, which again does not affect the manipulation or expression of the coding region.

Nucleic acids that hybridize to nucleic acids encoding anti-BCMA antibodies as described herein under moderately stringent conditions, preferably under highly stringent conditions are included in the description. Basic parameters affecting the selection of hybridization conditions and guidance on designing suitable conditions can be found in Sambrook, Fritsch and Maniatis (1989, Molecular Cloning: A Laboratory Manual, Cold Spring Harbor Laboratory Press, Cold Spring Harbor, NY, Chapters 9 and 11; and Current Protocols in Molecular Biology, 1995, edited by Ausubel et al., John Wiley & Sons, Inc., Sections 2.10 and 6.3-6.4).

As outlined herein, cassette mutagenesis or PCR mutagenesis or other techniques well known in the art are typically used for site-specific mutagenesis of nucleotides in DNA encoding anti-BCMA antibodies to generate DNA encoding variants, and thereafter the recombinant DNAs are expressed in cell culture to prepare variants according to the description. However, antigen-binding fragments comprising up to about (100-150 residues can be prepared by in vitro synthesis using established techniques.

As will be appreciated by those skilled in the art, due to the degeneracy of the genetic code, extremely large numbers of nucleic acids can be made, all of which encode the anti-BCMA antibodies or antigen-binding fragments thereof of the description. Thus, having identified a particular amino acid sequence, one of skill in the art can make any number of different nucleic acids by simply modifying the sequence of one or more codons in a manner that does not alter the amino acid sequence encoding the protein.

The present description also provides expression systems and constructs in the form of plasmids, expression vectors, transcription cassettes or expression cassettes comprising at least one polynucleotide as described above. Additionally, the present description provides host cells comprising the expression system or construct.

Expression vectors used in any host cell typically contain sequences for plasmid maintenance and for cloning and expression of exogenous nucleotide sequences. The sequences (collectively referred to in certain embodiments as "flanking sequences") typically include one or more of the following nucleotide sequences: a promoter, one or more enhancer sequences, an origin of replication, a transcription termination sequence, a complete intronic sequence containing donor- and receptor-splice sites, a sequence encoding leader sequence for polypeptide secretion, a ribosome binding site, polyadenylation sequence, a polylinker region for insertion of nucleic acids encoding antibodies to be expressed and optional marker elements. Each of these sequences is discussed below.

The vector may optionally contain a "tag" coding sequence, an oligonucleotide molecule located at the 5' or 3' end of the anti-BCMA antibody coding sequence; the oligonucleotide sequence encoding a polyhistidine (such as 6His) or another "tags", such as FLAG, HA (hemagglutinin influenza virus) or myc, are present in commercially available antibodies. This tag is typically fused to the polypeptide when it is expressed, and can serve as a means for affinity purification or detection of anti-BCMA antibodies from host cells. Affinity purification can be accomplished, for example, by column chromatography using an antibody against this tag as an affinity matrix. The label can be optionally removed later from purified anti-BCMA antibodies by various means such as the use of certain peptidases for cleavage.

Flanking sequences can be homologous (i.e., from the same species and/or strain as the host cell), heterologous (i.e., from a species other than the host cell species or strain), heterozygous (i.e., a combination of flanking sequences from more than one source), synthetic or natural. Similarly, the source of the flanking sequences can be any prokaryotic or eukaryotic organism, any vertebrate or invertebrate organisms or any plant, provided that the flanking sequences are functional and activable by host cell machinery.

The origin of replication is typically part of those prokaryotic expression vectors that are commercially available, and this origin facilitates the amplification of the vector in the host cell. If the chosen vector does not contain an origin of replication site, it can be chemically synthesized and ligated into the vector based on the known sequence. For example, origins of replication from plasmid pBR322 (New England Biolabs, Beverly, MA) are suitable for most Gram-negative bacteria, and various viral origins (e.g., SV40, polyoma, adenovirus, vesicular stomatitis virus (VSV) or papillomavirus, such as HPV or BPV) are suitable for cloning vectors in mammalian cells. Mammalian expression vectors generally do not require an origin of replication (e.g., often only the SV40 origin is used since it also contains the viral early promoter).

Transcription termination sequences are typically located at the 3' end of the polypeptide coding region to terminate transcription. Transcription termination sequences in prokaryotes are usually GC-rich fragments followed by poly-thymidylate sequences.

The selectable marker gene encodes a protein necessary for the survival and growth of host cells grown in selective media. Typical selectable marker genes encode proteins that (a) provide resistance to antibiotics or other toxins (e.g., ampicillin, tetracycline or kanamycin for prokaryotic host cells); (b) complement the auxotrophy of the cells; or (c) provide important nutrients not available from complexes or defined media. Specific selectable markers are the kanamycin resistance gene, the ampicillin resistance gene, and the tetracycline resistance gene. Advantageously, the neomycin resistance gene can also be used for selection in prokaryotic and eukaryotic host cells.

Ribosome binding sites are often necessary for translation initiation of mRNA and are characterized by Shine-Dalgarno sequences (prokaryotes) or Kozak sequences (eukaryotes). This element is typically located Y to the promoter and 5' to the coding sequence of the polypeptide to be expressed.

Expression and cloning vectors of the present description will typically contain a promoter recognized by the host organism and operably linked to the anti-BCMA antibody-encoding molecule. A promoter is a non-transcription sequence located upstream of the initiation codon of a structural gene (usually within about 100 to 1000 bp) that controls the transcription of the structural gene.

Suitable promoters for use with yeast hosts are also well known in the art. Yeast enhancers are advantageously used with yeast promoters. Suitable promoters for use with mammalian host cells are well known and include, but are not limited to, some promoters obtained from the viral genomes of such as polyoma virus, fowl pox virus, adenovirus (such as adenovirus 2), bovine papilloma virus, avian sarcoma virus, cytomegalovirus, retrovirus, hepatitis B virus and most preferably simian virus 40 (SV40). Other suitable mammalian promoters include heterologous mammalian promoters, such as heat shock protein (HSP) promoters and actin promoters.

Enhancer sequences can be inserted into vectors to increase transcription by higher eukaryotes of the DNA encoding the light or heavy chains that make up the anti-BCMA antibodies of the description. Enhancers are cis-acting elements of DNA that act on promoters to increase transcription and are usually around 10-300 bp in length. Enhancers are relatively orientation- and position-independent, and enhancers have been found at 5' and 3' positions in transcriptional units. Several enhancer sequences are known that are available from mammalian genes, such as enhancer sequences of globulin, elastase, albumin, alpha-fetoprotein, and insulin. However, enhancers from viruses are typically used. The SV40 enhancer, cytomegalovirus early promoter enhancer, polyoma enhancer, and adenovirus enhancer known in the art are exemplary enhancer elements for activating eukaryotic promoters.

The expression vector of the present description can be constructed from a starting vector such as a commercially available vector. Such vectors may or may not contain all desired flanking sequences. If one or more of the flanking sequences described herein are not already present in the vector, they can be obtained separately and linked to the vector. Methods for obtaining individual flanking sequences are well known to those skilled in the art.

After constructing the vector and inserting the nucleic acid molecule encoding the light chain, heavy chain, or light and heavy chain of the anti-BCMA antibody into the appropriate sites of the vector, the completed vector can be inserted into a suitable host cell for amplification and/or polypeptide expression. The expression vector for anti-BCMA antibodies can be transformed into host cells of choice by well-known methods including transfection, infection, calcium phosphate co-precipitation, electroporation, microinjection, lipofection, DEAE-dextran mediated transfection or other known techniques. The selected part of the method may vary with the type of host cell to be used.

When the host cells are grown under appropriate conditions such that they synthesize anti-BCMA antibodies, the anti-BCMA antibodies can then be collected from the culture medium (if the host cells secrete them into the culture medium) or directly from the host cells from which they were produced (if not secreted). Suitable host cells are as previously described.

Anti-BCMA Antibodies for Therapeutic Purposes

Anti-BCMA antibodies described herein can be used in the manufacture of medicaments for the treatment of the various conditions and diseases described herein, particularly diseases or conditions related to BCMA-expressing B cells (especially memory B cells and plasma B cells). These diseases, in particular conditions, relate to malignant plasma cells expressing relatively high levels of BCMA and monoclonal gammopathy of undetermined significance (MGUS) plasma cells. In some embodiments, the condition and disease is a B cell associated cancer, but is not limited to plasma cell leukemia; plasma cell tumor: B cell prolympho-cytic leukemia; hairy cell leukemia: B cell non-Hodgkin's lymphoma (NHL); acute myeloid leukemia (AML); chronic myelogenous leukemia (CML); acute lymphocytic leukemia (ALL): chronic lymphocytic leukemia (CLL): follicular lymphoma (including follicular non-Hodgkin's lymphoma) tumor type); Burkitt's lymphoma (endemic Burkitt's lymphoma; sporadic Burkitt's lymphoma); marginal zone lymphoma (mucosal-associated lymphoid tissue; MALT/MALToma; monocyte-like B cells lymphoma; splenic lymphoma with villous lymphocytes): mantle cell lymphoma; large cell lymphoma (diffuse large cell; diffuse mixed cell; immunoblastic lymphoma: primary mediastinal B-cell lymphoma; angiocentric lymphoma-lung B cells); small lymphocytic lymphoma (SLL): precursor B-lymphoblastic lymphoma; myeloid leukemia (granulocytic; myeloid; acute myeloid leukemia; chronic myelogenous leukemia; subacute myeloid leukemia; myeloid sarcoma; chloroma; granulocytic sarcoma; acute promyelocytic leukemia; acute myelomonocytic leukemia); Waldenström macroglobulinemia or other B-cell lymphoma.

In some embodiments, the conditions and diseases are B cell-related autoimmune disorders, including but not limited to systemic lupus erythematosus (SLE), rheumatoid arthritis (RA), multiple sclerosis (MS), Sjögren's syndrome, immune-mediated thrombocytopenia, hemolytic anemia, bullous pemphigoid, myasthenia gravis, type I diabetes, Graves' disease, Addison's disease, Pemphigus foliaceus, psoriasis, psoriatic arthritis and ankylosing spondylitis, etc.

Diagnostic Uses, Assays and Kits

Anti-BCMA antibodies of the description can be used in diagnostic assays, e.g., binding assays to detect and/or quantify BCMA expressed in tissues (such as bone marrow) or cells (such as plasma cells). Anti-BCMA antibodies can be used in further studies investigating the role of BCMA in disease. Anti-BCMA antibodies can be used to further study the function of BCMA in the formation of homo- and/or heteromeric receptor complexes and the function of said BCMA receptor complexes in disease.

Serum levels of BCMA can be prognostic and is a new tool to measure tumor burden (SanchezE et al, Serum B-cell maturation antigen is elevated in multiple myeloma and correlates with disease status and survival. Br J Haematology, 158, 727-38 (2012)). Embodiments of the description include diagnostic assays and kits to measure soluble BCMA as a potential surrogate for membrane-bound BCMA on tumor cells.

The anti-BCMA antibodies of the description can be used for diagnostic purposes to detect, diagnose, or monitor diseases and/or conditions associated with BCMA. The present description provides detection of the presence of BCMA in a sample using classical immunohistological methods known to those skilled in the art (e.g., Tijssen, 1993, Practice and Theory of Enzyme Immunoassays, Vol. 15, eds. RH Burdon and PH van Knippenberg, Elsevier, Amsterdam; Zola, 1987, Monoclonal Antibodies: A Manual of Techniques, pp. 147-158, CRC Press, Inc.; Jalkanen et al., 1985, J. Cell. Biol., 101: 976-985; Jalkanen et al., 1987, J. Cell Biol., 105: 3087-3096). Detection of BCMA can be performed in vivo or in vitro. Examples of methods suitable for detecting the presence of BCMA include ELISA, FACS, RIA, and the like.

Examples of methods suitable for detecting the presence of BCMA include ELISA, FACS, RIA, and the like. Suitable labeling groups include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorophores (e.g., FITC, rhodamine, lanthanide phosphors), enzymatic groups (e.g., horseradish peroxidase, beta-galactosidase, luciferase, alkaline phosphatase), chemiluminescent groups, biotinyl groups, or predetermined polypeptide epitopes recognized by secondary reporters (e.g., bright amino acid zipper pair sequences, binding sites for secondary antibodies, metal binding domains, epitope tags). In some embodiments, the labeling group is conjugated to the anti-BCMA antibody through the spacer of variable length to reduce potential steric hindrance.

Various methods for labeling proteins are known in the art and can be used to carry out the present description.

One aspect of the present description provides the identification of cells expressing BCMA. In a specific embodiment, the antibody is labeled with a labeling group and the binding of the labeled antibody to BCMA is detected. In another specific embodiment, the binding of the antibody to BCMA is detected in vivo. In another specific embodiment, the antibody-BCMA is isolated and measured using techniques known in the art.

Another aspect of the description provides detection of the presence of a test molecule that competes with an antibody of the description for binding to BCMA. An example of one such assay would involve detecting the amount of free antibody in a solution containing an amount of BCMA in the presence or absence of the test molecule. An increase in the amount of free antibody (i.e., antibody that does not bind BCMA) will indicate that the test molecule can compete with the antibody for binding to BCMA. In one embodiment, the antibody is labeled with a labeling group. Alternatively, the test molecule is labeled and the amount of free test molecule is monitored in the presence or absence of antibody.

Pharmaceutical Composition, Route of Administration

The present description provides pharmaceutical compositions comprising a therapeutically effective amount of one or more anti-BCMA antibodies of the present description together with a pharmaceutically acceptable diluent, carrier, solubilizer, emulsifier, preservative and/or adjuvant.

In certain embodiments, acceptable diluents, carriers, solubilizers, emulsifiers, preservatives and/or adjuvants, etc. in the pharmaceutical compositions are preferably nontoxic to recipients at the dosages and concentrations employed. In certain embodiments, pharmaceutical compositions may contain such substances for improving, maintaining, or preserving, for example, the pH, osmolarity, viscosity, clarity, color, isotonicity, odor, sterility, stability, dissolution, or the rate of release, absorption, or penetration of the composition. These substances are known from the prior art, e.g. see REMINGTON'S PHARMACEUTICAL SCIENCES, 18th Edition, A. R. Genrmo ed., 1990, Mack Publishing Company. The optimal pharmaceutical composition may be determined by the intended route of administration, mode of delivery, and desired dosage.

The pharmaceutical compositions of the present description may be selected for parenteral delivery. Alternatively, the composition may be selected for inhalation or delivery through the digestive tract, such as orally. The preparation of such pharmaceutically acceptable compositions is within the skill of the art.

Other pharmaceutical compositions will be apparent to those skilled in the art, including sustained or controlled release delivery formulations comprising anti-BCMA antibodies. Techniques for formulating a variety of other sustained or controlled delivery modes, such as liposomal vehicles, bioerodible microparticles or porous beads, and depot injections, are also known to those of skill in the art.

Pharmaceutical compositions for in vivo administration are usually provided in the form of sterile formulations. Sterilization is achieved by filtration through sterile filtration membranes. When the composition is lyophilized, it can be sterilized using this method before or after lyophilization and reconstitution. Compositions for parenteral administration may be in lyophilized form or stored in solution. Parenteral compositions are usually presented in containers with sterile access ports, such as intravenous solution strips or vials with a hypodermic needle pierceable stopper.

Once formulated, pharmaceutical compositions are stored in sterile vials as solutions, suspensions, gels, emulsions, solids, crystals, or as dehydrated or lyophilized powders. The formulations can be stored in ready-to-use form or reconstituted prior to administration (e.g., lyophilized). The present description also provides kits for producing single-dose administration units. The kits of the present description may each contain a first container with dried protein and a second container with an aqueous formulation. In certain embodiments of the present description, kits are provided containing single-chamber and multi-chambers pre-filled syringes (e.g., liquid syringes and lyophilized syringes).

The present description also provides methods of treating a patient (especially a patient with B cell-related diseases such as B cell-related cancer and autoimmune diseases) by administering the anti-BCMA antibody or antigen-binding fragment thereof or a pharmaceutical composition thereof according to any of the embodiments of the present description.

As used herein, the terms "patient", "subject", "individual", and "subject" are used interchangeably herein to include any organism, preferably an animal, more preferably a mammal (e.g., rat, mouse, dog, cats, rabbits, etc.), and most preferably humans. "Treatment" refers to the administration of a therapeutic regimen described herein to a subject to achieve at least one positive therapeutic effect (e.g., reduction in cancer cell number, reduction in tumor volume/burden, reduction in the rate of cancer cell infiltration into surrounding organs, or reduction in the rate of tumor metastasis or tumor growth). Treatment regimens that effectively treat a patient can vary depending on factors such as the patient's disease status/stage, age, weight, and the ability of the therapy to elicit an anticancer response in the subject.

The therapeutically effective amount of a pharmaceutical composition containing an anti-BCMA antibody or antigen-binding fragment thereof of the description to be employed will depend on, for example, the extent and objective of treatment. Those skilled in the art will appreciate that the appropriate dosage level for treatment will vary depending in part on the molecule being delivered, the indication, the route of administration and the size (body weight, body surface or organ size) and/or status (age and general health) of the patient. In certain embodiments, the clinician can titrate the dose and alter the route of administration to obtain optimal therapeutic effect.

In certain embodiments, the clinician can titrate the dose and alter the route of administration to obtain optimal therapeutic effect. Clinicians typically administer the compositions until a dosage is reached that achieves the desired effect. The composition may thus be administered as a single dose, or as two or more doses over time (which may or may not contain the same amount of the desired molecule), or as a continuous infusion through an implanted device or catheter.

The route of administration of the pharmaceutical composition is according to known methods, such as oral, intravenous, intraperitoneal, intracerebral (intraparenchymal), intracerebroventricular, intramuscular, intraocular, intraarterial, intra-portal-vein or intralesional route injection; sustained release systems or via implanted devices.

The present description will be illustrated by way of specific examples below. It should be understood that these examples are merely explanatory and is not intended to limit the scope of the present description. Unless otherwise specified, the methods and materials used in the examples are conventional materials and methods in the art.

Example 1: Immunization of Mice to Produce Monoclonal Antibodies Against Human BCMA The 6-week-old immunoglobulin-humanized mouse AceMouse was immunized with the expression vector pcDNA3.1(+) expressing the full-length human BCMA protein (sequence reference Uniprot database, No. Q02223). The fifth booster immunization was performed with a commercial recombinant human BCMA protein (Fc tag, Cat. No. CS79, Novoprotein) and standard Freund's complete adjuvant at a dose of 25 μg human recombinant BCMA protein per mouse.

Example 2: ELISA Detection of Immunized Mouse Serum

Human recombinant BCMA protein (Novoprotein, Cat. No. CS79), as antigen, was diluted with PBS to 0.5 ng/μl, and 100 μl/well of antigen was added to a 96-well flat-bottom ELISA plate (Maxisorp), sealed with cling film and placed at 4° C. overnight. After decanting the antigen the next day, the wells were washed once with PBS (200 μl/well). After decanting the PBS, the plate was patted dry on absorbent paper and added with 200 μl blocking solution (PBS containing 10% fetal bovine serum) to each well and blocked at room temperature for 2 hours. After blocking, pour off the blocking solution and pat dry on absorbent paper. Add 100 ml of diluent (PBS containing 5% fetal bovine serum) to dilute the serum concentration gradient, place at room temperature for 1 hour, then decante the sample and wash the solution three times with washing solution (PBS containing 0.05% Tween-20), and finally pour off the washing liquid and pat dry on absorbent paper. Add 100 μl of diluent to dilute HRP-conjugated goat anti-mouse IgG secondary antibody final concentration 0.4 μg/ml; Biolegend, product number 405306), place at room temperature for 1 hour, then pour off the liquid and wash 5 times with washing solution (200 μl/well), and finally pat dry on absorbent paper after decanting the wash solution. Add 50 μl/well of TMB-hydrogen peroxide urea solution (Thermo Scientific™, product number 34029) and place the substrate solution at room temperature in the dark for 3-5 minutes. Add 50 μl/well of 0.25M sulfuric acid to stop the reaction. The light absorption at 450 nm wavelength was detected on a multifunctional microplate reader. The results are shown in FIG. 1.

Example 3: Obtaining Hybridoma Cells from Immunized Mouse Spleen Cells Using Electrofusion Technology The Ag8 mouse myeloma cells were resuscitated in advance; the Ag8 mouse myeloma cells were counted on the day of fusion; the spleen of the BCMA mice after successful immunization was placed in the transport medium RPMI1640 and the cells in the isolated spleen were immediately extracted and counted for later use; the obtained spleen cells and myeloma cells were washed once with 10 ml RPMI 1640 respectively, and mixed according to the ratio of $4 \times 10^7$ spleen cells and $1 \times 10^7$ Ag8 mouse myeloma cells; after mixing, centrifuge at 200G for 5 minutes, discard the supernatant, and wash twice with 10 ml of fusion solution; centrifuge at 200G for 5 minutes at room temperature, discard the supernatant and add 2.5 ml of electrofusion buffer to resuspend the pellet; prepare a 15 ml centrifuge tube and add 4.8 ml of pre-warmed RPMI 1640 medium; the mixed cell suspension was added to the CUY497P2 electrode that had been sterilized with 75% alcohol and air-dried, and the cells were electrofused using an ECFG21 electrofusion apparatus according to the manufacturer's manual (manufactured by NEPAGENE, model ECFG21). After fusing, the cells were placed in 4.8 ml of preheated RPMI1640 medium in the incubator; resuspend the cells in HAT medium, and plate the cells on a 96-well flat bottom plate at $2\times10^5$ cells/well; place the 96-well plate in a 37° C. incubator for static culture, and observe daily. On the 10th day, the supernatant was taken for ELISA primary screening.

Example 4: Screening of Anti-Human BCMA Monoclonal Antibodies by ELISA

Dilute BCMA antigen (Novoprotein cat: CS79) with PBS to 0.5 ng/μl; add 100 μl/well of antigen to a 96-well flat-bottom ELISA plate (Maxisorp), seal with cling film, and store at 4° C. overnight; pour off the antigen the next day. After that, wash with PBS (200 μl/well), pour off the PBS, pat dry on absorbent paper and add 200 μl of blocking solution to each well and block at room temperature for 2 hours. After blocking, pour off the blocking solution and pat dry on absorbent paper; add 50 μl of HRP-conjugated goat anti-mouse IgG secondary antibody diluted in diluent, place at room temperature for 1 hour, then pour off the liquid and wash 5 times with washing solution (200 μl/well), finally pour off the washing solution and pat dry on absorbent paper; add 50 μl/well of TMB-hydrogen peroxide urea solution substrate solution and place it at room temperature for 3-5 minutes, add 50 μl/well of 0.25M sulfuric acid to stop the reaction, the optical density was measured by obtaining the absorbance with a 450 nm filter under a multifunctional microplate reader. The results are shown in Table 1 below.

TABLE 1

| Clone number | 7E11 | 8H7 | 11B10 | 11G1 | 15A7 | 15H6 |
|---|---|---|---|---|---|---|
| OD450 | 2.299 | 2.706 | 2.551 | 2.713 | 2.117 | 2.491 |
| Clone number | 18D10 | 20A9 | 23C4 | 27A7 | 31F5 | 20A2 |
| OD450 | 2.402 | 2.2 | 2.86 | 2.588 | 3.003 | 1.309 |

Note: The dilution multiple of hybridoma supernatant for ELISA screening of clones was 1:50 except that the dilution multiple of hybridoma supernatant was 1:100 during ELISA screening of 20A2.

Figure 2:
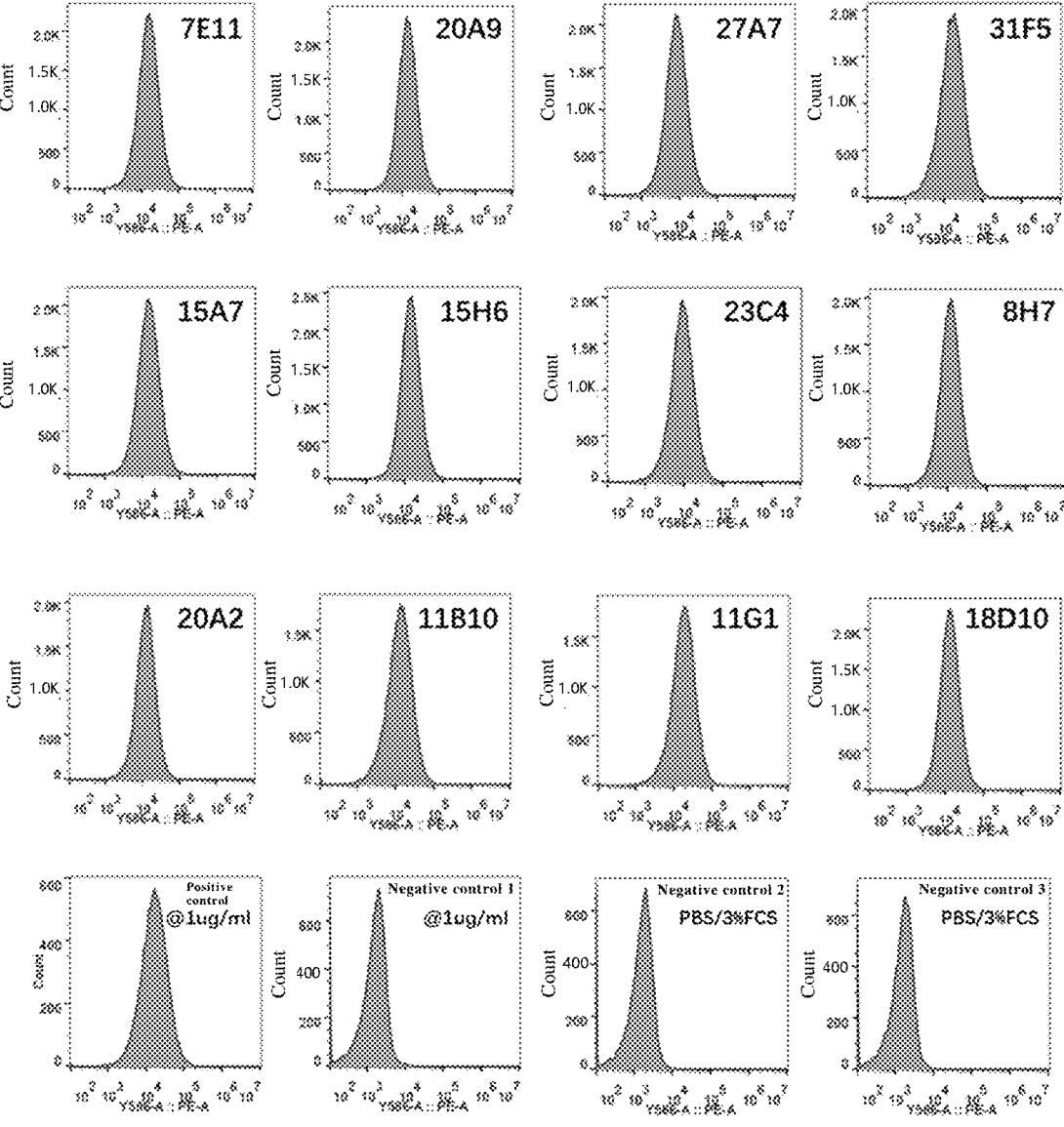
FIG. 2 shows flow cytometry analysis of anti-human BCMA monoclonal antibody binding to BCMA expressed on the surface of U266 cells in Example 5.

Example 5: Detection of Anti-Human BCMA Antibody Binding to U266 Cell Surface BCMA Analysis by Flow Cytometry The U266 cells were collected by centrifugation at 200G, washed once with PBS containing 3% FCS, and then resuspended in 1.5 ml of PBS containing 3% FCS. 25 μl of cell suspension ($2.5\times10^5$) and 75 μl ml of samples (the BCMA hybridoma cell culture supernatant obtained in Example 3) were added to each well of a 96-well plate sequentially. Besides, and add 75 ml of anti-BCMA antibody (clone 19F2, Biolegend, final concentration 1 mg/ml) to the positive control wells; 75 μl IgG2a isotype control (clone MG2a-53, Biolegend, final concentration 1 μg/ml) was added to negative control well; 75 μl of PBS containing 3% FCS was added to negative control well 2 and negative control well 3, incubate in a refrigerator at 4° C. for 1 hour, then wash twice with PBS containing 3% FCS; after decanting the supernatant, add 50 μl of 500 ng/ml concentration of secondary antibody (ebioscience, goat anti-mouse IgG-PE, Cat. No. 12-4010-82) to each well; ml besides the negative control well 3 in which 50 ml of PBS containing 3% FCS was added instead, then place the plate in a 4° C. refrigerator. After incubation in the dark for 30 minutes, the cells were washed twice with PBS containing 3% FCS, and finally the cells were resuspended in 50 μl of PBS containing 3% FCS for detection by flow cytometry. The results are shown in FIG. 2.

Figure 3:
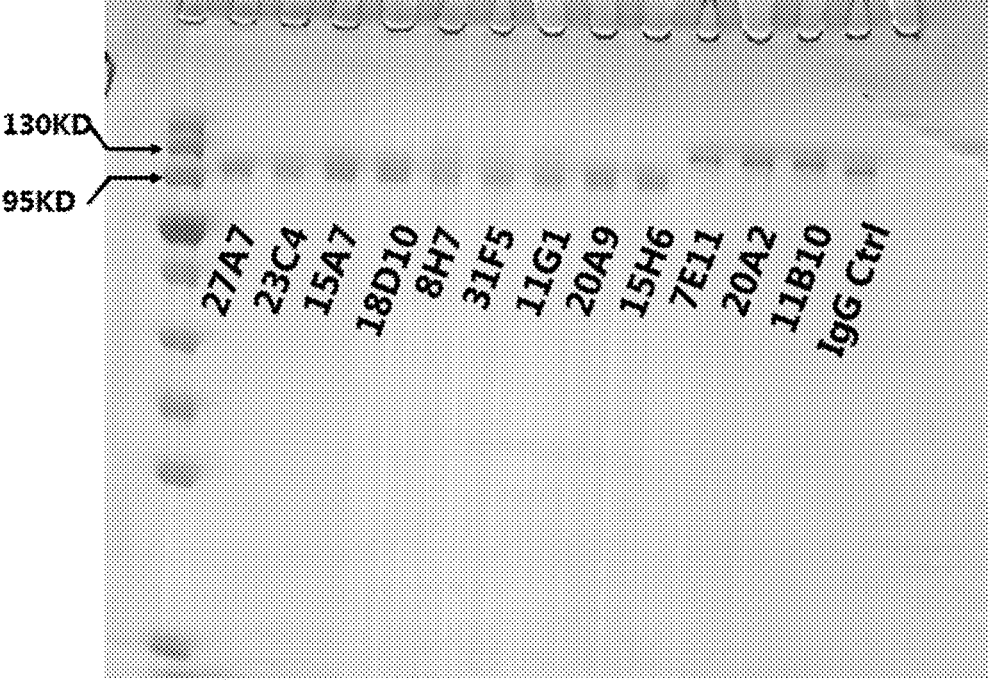
FIG. 3 shows the SDS-PAGE gel electrophoresis analysis of each anti-human BCMA monoclonal antibody purified in Example 6.

Example 6: Analysis and Purification of Anti-Human BCMA Monoclonal Antibody from the BCMA Hybridoma Supernatant Obtained in Example 3 by Using rProteinG Agarose-Based Magnetic Microspheres 8 ml of the hybridoma supernatant was obtained from the BCMA hybridoma cell culture obtained in Example 3, and 200 μl of rProteinG agarose-based magnetic microsphere suspension was added (Smart-Lifesciences, product number SM004C). Then place the centrifuge tube in a flip mixer and gently invert the centrifuge tube for 1 hour at room temperature; add 5 times the volume of magnetic beads to the centrifuge tube, wash twice, add 600 ml of eluent, and blow with a pipette. After blowing 5 times, place the centrifuge tube in a flip mixer at room temperature for 10 minutes to elute. After the solution becomes clear, aspirate the supernatant and collect the elution fraction, which is the target antigen. Collect the supernatant to a new centrifuge tube, and immediately add 60 ml of neutralizing solution to adjust the pH of the elution fraction to 7.0-8.0; take a small amount of purified antibody and dilute it to 200 mg/ml, and add 10 ml of antibody solution to 2.5 ml of 5× protein loading buffer (non-denaturing) (Sangon Biotech, product number C506032), after mixing, and three pre-stained prestained protein Marker (Sangon Biotech, product number C510010) are added to 12% Tris-Glycine electrophoresis precast gel in the sample wells (Sangon Biotech, Product No. C661102). The precast gel has been placed in an electrophoresis tank filled with Tris-SDS running buffer (Sangon Biotech, Product No. C520001), and electrophorese according to the standard procedure of the precast gel manufacturer. After electrophoresis, the samples were stained with a universal protein staining solution (Sangon Biotech, product number C516024) for 2 hours, and then the images were scanned after elution. The results are shown in FIG. 3. The remaining purified mAb for later functional analysis was stored at −20° C.

Example 7: Acquisition of Candidate Antibody Sequences

Cultured candidate hybridoma cells were collected by centrifugation at 1000 rpm, and total RNA is extracted with Trizol reagent as the template for the subsequent synthesis of first-strand cDNA which served as the template to amplify the variable region DNA sequence corresponding to the hybridoma cells (Jones and Bendig, 1991). In a 50 μl reaction system, add 1 μl cDNA, 5 μl 10×PCR buffer, 1 μl forward and reverse primers (25 pmol), 1 μl dNTP, 1 μl 25 mmol PL MgCl$_2$, 39 μl H$_2$O, and pre-denature at 95° C. for 10 min, add 1 μl of Taq enzyme, enter the temperature cycle, and carry out PCR amplification. The reaction conditions are denaturation at 94° C. for 1 min, annealing at 58° C. for 1 min, extension at 72° C. for 15 s, a total of 32 cycles, and then incubation at 72° C. for 10 min.

After sequencing the amplified products, the antibody sequences of the candidate hybridomas are obtained as follows:

7E11
VH(SEQ ID NO: 10):
EVQLVESGGGLVQPGGSLRLSCAASGFTFSYYDMHWVRQGTGKGLEWV
SGIGTSGDTYYPDSVKGRFTISREN<u>A</u>KNSLNLQMNSLRDGDTAMYYCARG
PYYYNSSGYYSYDALDIWGQGTMVTVTS

VL(SEQ ID NO: 11):
DIVMTQSPLSLSVTPGEPASISCRSSQSLLHSNGYNYLDWYLQKPGQSPQ
LLIYLGSNRASGVPDRFSGSGSGTDFTLKISRVEAEGVGVYYCMQALQTPY
TFGQGTKLEIK

HCDR1: GFTFSYYD(SEQ ID NO: 12)

HCDR2: IGTSGDT(SEQ ID NO: 13)

HCDR3: ARGPYYYNSSGYYSYDALDI(SEQ ID NO: 14)

LCDR1: QSLLHSNGYNY(SEQ ID NO: 15)

LCDR2: LGS(SEQ ID NO: 16)

LCDR3: MQALQTPYT(SEQ ID NO: 17)

8H7
VH(SEQ ID NO: 18):
EVQLVESGGGLVQPGRSLRISCAGSGFTFDDYAMHWVRQAPGKGLEWV
SGISWNSDTIAYADSVKGRFTISRD<u>N</u>AKNSLYLQMNSLRAEDTALYYCAKV
SGAVFDYCGQGTQVTVSS

VL(SEQ ID NO: 19):
DIQMTQSPSSLSASVKDRVIITCRASQSIHSYLNWYQQKPGKAPKLLIYSA
SSLQSGVPSRFSGSGSGTDFTLTISSLQPEDFATYYCQQSFSIPYTFGQGTKLE
IK

HCDR1: GFTFDDYA(SEQ ID NO: 20)

HCDR2: ISWNSDTI(SEQ ID NO: 21)

HCDR3: AKVSGAVFDY(SEQ ID NO: 22)

LCDR1: QSIHSY(SEQ ID NO: 23)

LCDR2: SAS(SEQ ID NO: 24)

LCDR3: QQSFSIPYT(SEQ ID NO: 25)

11B10
VH(SEQ ID NO: 26):
QVQLVQSGAEVKKPGASVKVSCKASGYTFTSYAMHWVRQAPGQRLEW
MGWINTGNGNTKYSQKFQGRVTITRDTSASTAYMELSSLRSEDTAVYYCA
RGGSITGNIFYYYYMDVWGKGTTVTVAS

VL(SEQ ID NO: 27):
DIVVTQSPDSLAVSLGERATINCKSSQSFLSSSNNKNYLAWYQQKPGQPP
KLLIYWASTRESGVPDRFSGSGSGTDFTLTISSLQAEDVAVYYCQQYYSIPFT
FGPGTKVDIK

HCDR1: GYTFTSYA(SEQ ID NO: 28)

HCDR2: INTGNGNT(SEQ ID NO: 29)

HCDR3: ARGGSITGNIFYYYYMDV(SEQ ID NO: 30)

LCDR1: QSFLSSSNNKNY(SEQ ID NO: 31)

LCDR2: WAS(SEQ ID NO: 32)

LCDR3: QQYYSIPFT(SEQ ID NO: 33)

11G1
VH(SEQ ID NO: 34):
EVQLVESGGGLVQPGRSLRLSCEASGFTFDDYAMHWVRQPPGKGLEWV
SGISWNSDNIGYADSVKGRFTISRD<u>N</u>AKNSLYLQMNSLRAEDTALYYCAKI
QSGSSFDYWGQGTLVTVSS

VL(SEQ ID NO: 35:
DIQMTQSPSSLSASVGDRVTITCRASQSIINFLNWYQQKPGKAPKLLIYGA
SNLQSGVPSRFSGSGSGTDFTLTISSLQPEDFATYCCQQSSSIPLTFGGGTKVE
IK

-continued

HCDR1: GFTFDDYA(SEQ ID NO: 36)

HCDR2: ISWNSDNI(SEQ ID NO: 37)

HCDR3: AKIQSGSSFDY(SEQ ID NO: 38)

LCDR1: QSIINF(SEQ ID NO: 39)

LCDR2: GAS(SEQ ID NO: 40)

LCDR3: QQSSSIPLT(SEQ ID NO: 41)

15A7
VH(SEQ ID NO: 42):
EVQLVESGGGLVQPGGSLRLSCEASGFTFDDCAMHWVRQTPGKGLEWV
SGISWNSDTMGYADSVKGRFIISRDNAKNSLYLQMNSLRVEDTALYHCTRV
RAAVFDYWGQGVLVTVSS

VL(SEQ ID NO: 43):
DIHMTQSPSSLSASVGDRVTITCRASQSISSYLNWFQQKPGKAPTVLIYAA
SSLQSGVSSRFSGRGSGADFTLTISSLQPEDFASYFCQQSFSPLYIFGQGTKV
EIK

HCDR1: GFTFDDCA(SEQ ID NO: 44)

HCDR2: ISWNSDTM(SEQ ID NO: 45)

HCDR3: TRVRAAVFDY(SEQ ID NO: 46)

LCDR1: QSISSY(SEQ ID NO: 47)

LCDR2: AAS(SEQ ID NO: 48)

LCDR3: QQSFSPLYI(SEQ ID NO: 49)

15H6
VH(SEQ ID NO: 50):
QVQLVQSGAEVKKPGASAKVSCKASGYTFTSYAMQWVRQAPGQRLEW
MGWINAGNGNTKYSQKFQGRVTITRDTSASTAYMELSSLRSEDTAVYYCA
RGGRLELDIYYYFYYMDVWGKGTTVTVSS

VL(SEQ ID NO: 51):
DIVMSQSPDSLAVSLGERTTINCKSSQSVLHSSQNKNYLAWYQQKPGQPP
NPLIHWASTRESGVPDRFSGSGSGTDFTLTISSLQAEDVAVYYCQQYYRVPF
TFGPGTKVDIK

HCDR1: GYTFTSYA(SEQ ID NO: 52)

HCDR2: INAGNGNT(SEQ ID NO: 53)

HCDR3: ARGGRLELDIYYYFYYMDV(SEQ ID NO: 54)

LCDR1: QSVLHSSQNKNY(SEQ ID NO: 55)

LCDR2: WAS(SEQ ID NO: 56)

LCDR3: QQYYRVPFT(SEQ ID NO: 57)

18D10
VH(SEQ ID NO: 58):
EVRLVESGGGLVQPGRSLRLSCAASGFTSNDYAMHWVRQAPGRGLEWV
SGISWNSDSIGYADSVKGRFTISRDNAKNSLYLQMNSLRTEDTALYYCATVV
SAYFDYWGQGTLVTVSS

VL(SEQ ID NO: 59):
DIQMTQSPSSLSASVGDRVTITCRTSQSISTYLNWYQQKPGKAPKLLIYAA
SSLKSGVPSRFSGSGSGTDFTLTISSLQPEDFATYFCQGSYIIPLTFGGGTRVEI
K

HCDR1: GFTSNDYA(SEQ ID NO: 60)

HCDR2: ISWNSDSI(SEQ ID NO: 61)

HCDR3: ATVVSAYFDY(SEQ ID NO: 62)

LCDR1: QSISTY(SEQ ID NO: 63)

LCDR2: AAS(SEQ ID NO: 64)

LCDR3: QGSYIIPLT(SEQ ID NO: 65)

-continued

20A2

VH(SEQ ID NO: 66):
QIQLVQSGAEVKKPGASVKVSCKASGYTFTAYYLHWVRQSPGHGLEWM
GRIYPNSGDTNYAQKFQGRVTMTRDTSINTAYMELSRLRSDDTALYYC**ARG
FNWNYEGGFDI**WGQGTMVTVSS

VL(SEQ ID NO: 67):
DVVMTQSPLSLSVTLGQPASISCRSGQSLVYSDGNTYLNWFQQRPGQSPR
RLIYKLSSRDSGVPDRFSGSGSGTDFTLKISRMEAEDVGVYYC**MQRTHWP
PT**FGQGTKVEIK

HCDR1: GYTFTAYY(SEQ ID NO: 68)

HCDR2: IYPNSGDT(SEQ ID NO: 69)

HCDR3: ARGFNWNYEGGFDI(SEQ ID NO: 70)

LCDR1: QSLVYSDGNTY(SEQ ID NO: 71)

LCDR2: KLS(SEQ ID NO: 72)

LCDR3: MQRTHWPPT(SEQ ID NO: 73)

20A9

VH(SEQ ID NO: 74):
QVQLVQSGAEVKKPGASAKVSCKASGYTFTSYAMQWVRQAPGQRLEW
MGWINAGNGNIKYSQKFQGRVTITRDTSASTAYMELSSLRSEDTAVYYC**AR
GGRLELDVYYYFYYMDV**WGKGTTVTVSS

VL(SEQ ID NO: 75):
DIVMSQSPDSLAVSLGERTTINCKSSQSVLHSSQNKNYLAWYQQKPGQPP
NPLIHWASTRESGVPDRFSGSGSGTDFTLTISSLQAEDVAVYYC**QQYYRVPF
T**FGPGTKVDIK

HCDR1: GYTFTSYA(SEQ ID NO: 76)

HCDR2: INAGNGNI(SEQ ID NO: 77)

HCDR3: ARGGRLELDVYYYFYYMDV(SEQ ID NO: 78)

LCDR1: QSVLHSSQNKNY(SEQ ID NO: 79)

LCDR2: WAS(SEQ ID NO: 80)

LCDR3: QQYYRVPFT(SEQ ID NO: 81)

23C4

VH(SEQ ID NO: 82):
EVQLVESGGGLVQPGRSLRLSCAASGFTFADHAMHWVRQAPGKGLEW
VSGISWNSDHIGYADSVKGRFTISRDNAKNSLYLQMNSLRPEDTALYYC**AK
DIFSPTGDGY**WGQGTLVTVSS

VL(SEQ ID NO: 83):
DIQMTQSPSSLSASVGDRVTITCRASQDIRNNLGWFQQKPGKTPKRLIY**A
ASSLQSGVPSRFSGSGSGTEFTLIISSLQPEDFATYYCLHHNSYPPT**FGQGTK
VEIK

HCDR1: GFTFADHA(SEQ ID NO: 84)

HCDR2: ISWNSDHI(SEQ ID NO: 85)

HCDR3: AKDIFSPTGDGY(SEQ ID NO: 86)

LCDR1: QDIRNN(SEQ ID NO: 87)

LCDR2: AAS(SEQ ID NO: 88)

LCDR3: LHHNSYPPT(SEQ ID NO: 89)

27A7

VH(SEQ ID NO: 90):
EVQLVESGGGLVQPGRSLRLSCAASGFTFDDHAMHWVRQAPGKGLEW
VSGISWNSVHIGYADSVKGRFTISRDNAKNSLYLQMNSLRAEDTALYYC**AK
DIFSPTGDDY**WGQGTLVTVSS

VL(SEQ ID NO: 91):
DIQMTQSPSSLSASVGDRVTITCRASQDIRNNLGWFQQKPGKTPKRLIY**A
ASSLQSGVPSRFSGSGSGTEFTLTISSLQPEDFATYYCLHHNSYPPT**FGQGTK
VEIK

```
                                    -continued
HCDR1: GFTFDDHA(SEQ ID NO: 92)

HCDR2: ISWNSVHI(SEQ ID NO: 93)

HCDR3: AKDIFSPTGDDY(SEQ ID NO: 94)

LCDR1: QDIRNN(SEQ ID NO: 95)

LCDR2: AAS(SEQ ID NO: 96)

LCDR3: LHHNSYPPT(SEQ ID NO: 97)

31F5
VH(SEQ ID NO: 98):
EVQLVESGGGLVQPGRSLRLSCAASGFTFDDYAMHWVRQAPGKGLEWV
SGISWNSDNIAYADSVKGRFTISRDNAENSLYLQMNSLRTEDTAIYYCAKVA
AATFDYRGQGTLVTVSS

VL(SEQ ID NO: 99):
DIQMTQSPSSLSASVGDRVTITCRASQSISSYLNWYQQKPGKAPKLLIFAA
SSLQSGVPSRFSGSGSGTDFTLTISSLQPEDFATYSCQQSFSIPFTFGPGTKVDI
K

HCDR1: GFTFDDYA(SEQ ID NO: 100)

HCDR2: ISWNSDNI(SEQ ID NO: 101)

HCDR3: AKVAAATFDY(SEQ ID NO: 102)

LCDR1: QSISSY(SEQ ID NO: 103)

LCDR2: AAS(SEQ ID NO: 104)

LCDR3: QQSFSIPFT(SEQ ID NO: 105)
```

The heavy chain constant region sequence of the above-mentioned antibody is:

```
                                (SEQ ID NO: 106)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK;
```

The light chain constant region sequence is:

```
                                (SEQ ID NO: 107)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.
```

Example 8: Affinity Analysis of Anti-Human BCMA Monoclonal Antibody Binding to Human BCMA The kit, consumables and instruments used in this example were purchased from GE Healthcare; According to the instructions provided, human BCMA antigen (6His tag, product number CC28, Novoprotein) is conjugated to the chip surface, and then HBS-EP+ buffer solution is double-diluted to prepare different concentrations of the antibody to be analyzed, and meanwhile set the 0 concentration point and the quality control concentration point; According to the manufacturer's standard setting procedure of Biacore T200, the flow cell that captures ligand is used as the detection channel, the flow cell of un-captured ligand as the reference channel, and the HBS-EP+ buffer solution as the mobile phase, and different concentrations of the antibody solution to be analyzed are injected respectively; The SPR signal is collected by the Biacore T200 Control software, and then the data is processed by the Biacore T200 Evaluation analysis software; Finally, the Ka, Kd and KD values are calculated for the kinetic analysis or steady-state analysis of the obtained kinetic curves, and the results are shown in Table. 2.

TABLE 2

| Clone number | Ka (1/Ms) | Kd (1/s) | KD (pM) | Clone number | Ka (1/Ms) | Kd (1/s) | KD (pM) |
|---|---|---|---|---|---|---|---|
| 20A9 | 5.726E+5 | 2.342E−5 | 40.91 | 11B10 | 1.061E+6 | 2.685E−4 | 253.10 |
| 23C4 | 4.810E+5 | 7.015E−5 | 145.80 | 11G1 | 4.715E+5 | 1.627E−5 | 34.50 |
| 27A7 | 6.181E+6 | 7.222E−5 | 11.69 | 15A7 | 4.801E+5 | 6.021E−5 | 125.40 |
| 31F5 | 5.764E+5 | 2.781E−5 | 48.25 | 15H6 | 4.828E+5 | 4.275E−5 | 88.54 |
| 7E11 | 5.101E+5 | 2.572E−5 | 50.42 | 18D10 | 5.095E+5 | 2.431E−5 | 47.72 |
| 8H7 | 6.122E+5 | 1.111E−5 | 18.14 | 20A2 | 8.068E+5 | 5.294E−5 | 65.62 |

We claim:

1. An anti-B cell maturation antigen (anti-BCMA) antibody or an antigen-binding fragment thereof, wherein the anti-BCMA antibody comprises a variable heavy chain domain (VH) comprising a CDR1 (HCDR1) as set forth in SEQ ID NO:68, a CDR2 (HCDR2) as set forth in SEQ ID NO:69, and a CDR3 (HCDR3) as set forth in SEQ ID NO:70, and a variable light chain domain (VL) comprising a CDR1 (LCDR1) as set forth in SEQ ID NO:71, a CDR2 (LCDR2) as set forth in SEQ ID NO:72, and a CDR3 (LCDR3) as set forth in SEQ ID NO:73.

2. The anti-BCMA antibody or the antigen-binding fragment thereof of claim 1, wherein the anti-BCMA antibody is a chimeric antibody or a complete human antibody.

3. The anti-BCMA antibody or the antigen-binding fragment thereof of claim 2, wherein the anti-BCMA antibody is a complete human antibody.

4. A pharmaceutical composition, wherein the pharmaceutical composition comprises the anti-BCMA antibody or the antigen-binding fragment thereof of claim 1, and a pharmaceutically acceptable excipient or carrier.

5. The anti-BCMA antibody or the antigen-binding fragment thereof of claim 1, wherein the amino acid sequence of the VH of the anti-BCMA antibody is as set forth in SEQ ID NO: 66 and the amino acid sequence of the VL of the anti-BCMA antibody is as set forth in SEQ ID NO: 67.

6. The anti-BCMA antibody or the antigen-binding fragment thereof of claim 1, wherein the heavy chain constant region sequence of the BCMA antibody is set forth in SEQ ID NO: 106, and/or the light chain constant region sequence is set forth in SEQ ID NO: 107.

* * * * *

SEQUENCE LISTING

<160> NUMBER OF SEQ ID NOS: 107

<210> SEQ ID NO 1
<211> LENGTH: 8
<212> TYPE: PRT
<213> ORGANISM: Artificial Sequence
<220> FEATURE:
<223> OTHER INFORMATION: HCDR1
<220> FEATURE:
<221> NAME/KEY: MUTAGEN
<222> LOCATION: (2)..(2)
<223> OTHER INFORMATION: Xaa is F or Y
<220> FEATURE:
<221> NAME/KEY: MUTAGEN
<222> LOCATION: (4)..(4)
<223> OTHER INFORMATION: Xaa is F or S
<220> FEATURE:
<221> NAME/KEY: MUTAGEN
<222> LOCATION: (5)..(5)
<223> OTHER INFORMATION: Xaa is S, D, T, N or A
<220> FEATURE:
<221> NAME/KEY: MUTAGEN
<222> LOCATION: (6)..(6)
<223> OTHER INFORMATION: Xaa is Y, D, S or A
<220> FEATURE:
<221> NAME/KEY: MUTAGEN
<222> LOCATION: (7)..(7)
<223> OTHER INFORMATION: Xaa is Y, C or H
<220> FEATURE:
<221> NAME/KEY: MUTAGEN
<222> LOCATION: (8)..(8)
<223> OTHER INFORMATION: Xaa is D, A or Y

<400> SEQUENCE: 1

Gly Xaa Thr Xaa Xaa Xaa Xaa Xaa
1               5

<210> SEQ ID NO 2
<211> LENGTH: 8
<212> TYPE: PRT
<213> ORGANISM: Artificial Sequence
<220> FEATURE:
<223> OTHER INFORMATION: HCDR2
<220> FEATURE:
<221> NAME/KEY: MUTAGEN
<222> LOCATION: (2)..(2)
<223> OTHER INFORMATION: Xaa is S, N or Y
<220> FEATURE:
<221> NAME/KEY: MUTAGEN
<222> LOCATION: (3)..(3)
<223> OTHER INFORMATION: Xaa is W, T, A or P
<220> FEATURE:
<221> NAME/KEY: MUTAGEN
<222> LOCATION: (4)..(4)
<223> OTHER INFORMATION: Xaa is N or G
<220> FEATURE:
<221> NAME/KEY: MUTAGEN
<222> LOCATION: (5)..(5)
<223> OTHER INFORMATION: Xaa is S or N
<220> FEATURE:
<221> NAME/KEY: MUTAGEN
<222> LOCATION: (6)..(6)
<223> OTHER INFORMATION: Xaa is D, G or V
<220> FEATURE:
<221> NAME/KEY: MUTAGEN
<222> LOCATION: (7)..(7)
<223> OTHER INFORMATION: Xaa is T, N, S, D or H
<220> FEATURE:
<221> NAME/KEY: MUTAGEN
<222> LOCATION: (8)..(8)
<223> OTHER INFORMATION: Xaa is I, M or T

<400> SEQUENCE: 2

Ile Xaa Xaa Xaa Xaa Xaa Xaa Xaa
1               5

```
<210> SEQ ID NO 3
<211> LENGTH: 19
<212> TYPE: PRT
<213> ORGANISM: Artificial Sequence
<220> FEATURE:
<223> OTHER INFORMATION: HCDR3
<220> FEATURE:
<221> NAME/KEY: MUTAGEN
<222> LOCATION: (5)..(5)
<223> OTHER INFORMATION: Xaa is S or R
<220> FEATURE:
<221> NAME/KEY: MUTAGEN
<222> LOCATION: (6)..(6)
<223> OTHER INFORMATION: Xaa is I or L
<220> FEATURE:
<221> NAME/KEY: MUTAGEN
<222> LOCATION: (7)..(7)
<223> OTHER INFORMATION: Xaa is T or E
<220> FEATURE:
<221> NAME/KEY: MUTAGEN
<222> LOCATION: (8)..(8)
<223> OTHER INFORMATION: Xaa is G or L
<220> FEATURE:
<221> NAME/KEY: MUTAGEN
<222> LOCATION: (9)..(9)
<223> OTHER INFORMATION: Xaa is N or D
<220> FEATURE:
<221> NAME/KEY: MUTAGEN
<222> LOCATION: (10)..(10)
<223> OTHER INFORMATION: Xaa is I or V
<220> FEATURE:
<221> NAME/KEY: MUTAGEN
<222> LOCATION: (11)..(11)
<223> OTHER INFORMATION: Xaa is F or Y
<220> FEATURE:
<221> NAME/KEY: MUTAGEN
<222> LOCATION: (14)..(14)
<223> OTHER INFORMATION: Xaa is F or Y

<400> SEQUENCE: 3

Ala Arg Gly Gly Xaa Xaa Xaa Xaa Xaa Xaa Xaa Tyr Tyr Xaa Tyr Tyr
1               5                   10                  15

Met Asp Val

<210> SEQ ID NO 4
<211> LENGTH: 10
<212> TYPE: PRT
<213> ORGANISM: Artificial Sequence
<220> FEATURE:
<223> OTHER INFORMATION: HCDR3
<220> FEATURE:
<221> NAME/KEY: MUTAGEN
<222> LOCATION: (1)..(1)
<223> OTHER INFORMATION: Xaa is A or T
<220> FEATURE:
<221> NAME/KEY: MUTAGEN
<222> LOCATION: (2)..(2)
<223> OTHER INFORMATION: Xaa is K, R or T
<220> FEATURE:
<221> NAME/KEY: MUTAGEN
<222> LOCATION: (3)..(3)
<223> OTHER INFORMATION: Xaa is V or IQ
<220> FEATURE:
<221> NAME/KEY: MUTAGEN
<222> LOCATION: (4)..(4)
<223> OTHER INFORMATION: Xaa is S, V or A
<220> FEATURE:
<221> NAME/KEY: MUTAGEN
<222> LOCATION: (5)..(5)
<223> OTHER INFORMATION: Xaa is G, S or A
<220> FEATURE:
<221> NAME/KEY: MUTAGEN
<222> LOCATION: (6)..(6)
<223> OTHER INFORMATION: Xaa is A or S
```

-continued

```
<220> FEATURE:
<221> NAME/KEY: MUTAGEN
<222> LOCATION: (7)..(7)
<223> OTHER INFORMATION: Xaa is V, S, Y or T

<400> SEQUENCE: 4

Xaa Xaa Xaa Xaa Xaa Xaa Xaa Phe Asp Tyr
1               5                   10

<210> SEQ ID NO 5
<211> LENGTH: 12
<212> TYPE: PRT
<213> ORGANISM: Artificial Sequence
<220> FEATURE:
<223> OTHER INFORMATION: HCDR3
<220> FEATURE:
<221> NAME/KEY: MUTAGEN
<222> LOCATION: (11)..(11)
<223> OTHER INFORMATION: Xaa is G or D
<220> FEATURE:
<221> NAME/KEY: UNSURE
<222> LOCATION: (11)..(11)
<223> OTHER INFORMATION: The 'Xaa' at location 11 stands for Gln, Arg,
      Pro, or Leu.

<400> SEQUENCE: 5

Ala Lys Asp Ile Phe Ser Pro Thr Gly Asp Xaa Tyr
1               5                   10

<210> SEQ ID NO 6
<211> LENGTH: 6
<212> TYPE: PRT
<213> ORGANISM: Artificial Sequence
<220> FEATURE:
<223> OTHER INFORMATION: LCDR1
<220> FEATURE:
<221> NAME/KEY: MUTAGEN
<222> LOCATION: (2)..(2)
<223> OTHER INFORMATION: Xaa is S or D
<220> FEATURE:
<221> NAME/KEY: MUTAGEN
<222> LOCATION: (4)..(4)
<223> OTHER INFORMATION: Xaa is H, I, S or R
<220> FEATURE:
<221> NAME/KEY: MUTAGEN
<222> LOCATION: (5)..(5)
<223> OTHER INFORMATION: Xaa is S, N, S or T
<220> FEATURE:
<221> NAME/KEY: MUTAGEN
<222> LOCATION: (6)..(6)
<223> OTHER INFORMATION: Xaa is Y, F or N

<400> SEQUENCE: 6

Gln Xaa Ile Xaa Xaa Xaa
1               5

<210> SEQ ID NO 7
<211> LENGTH: 11
<212> TYPE: PRT
<213> ORGANISM: Artificial Sequence
<220> FEATURE:
<223> OTHER INFORMATION: LCDR1
<220> FEATURE:
<221> NAME/KEY: MUTAGEN
<222> LOCATION: (3)..(3)
<223> OTHER INFORMATION: Xaa is L, V or F
<220> FEATURE:
<221> NAME/KEY: MUTAGEN
<222> LOCATION: (4)..(4)
<223> OTHER INFORMATION: Xaa is L or V
<220> FEATURE:
<221> NAME/KEY: MUTAGEN
<222> LOCATION: (5)..(5)
```

```
<223> OTHER INFORMATION: Xaa is H, Y or S
<220> FEATURE:
<221> NAME/KEY: MUTAGEN
<222> LOCATION: (6)..(6)
<223> OTHER INFORMATION: Xaa is S or SS
<220> FEATURE:
<221> NAME/KEY: MUTAGEN
<222> LOCATION: (7)..(7)
<223> OTHER INFORMATION: Xaa is N, Q or D
<220> FEATURE:
<221> NAME/KEY: MUTAGEN
<222> LOCATION: (8)..(8)
<223> OTHER INFORMATION: Xaa is G or N
<220> FEATURE:
<221> NAME/KEY: MUTAGEN
<222> LOCATION: (9)..(9)
<223> OTHER INFORMATION: Xaa is Y, K or N
<220> FEATURE:
<221> NAME/KEY: MUTAGEN
<222> LOCATION: (10)..(10)
<223> OTHER INFORMATION: Xaa is N or T

<400> SEQUENCE: 7

Gln Ser Xaa Xaa Xaa Xaa Xaa Xaa Xaa Xaa Tyr
1               5                   10

<210> SEQ ID NO 8
<211> LENGTH: 3
<212> TYPE: PRT
<213> ORGANISM: Artificial Sequence
<220> FEATURE:
<223> OTHER INFORMATION: LCDR2
<220> FEATURE:
<221> NAME/KEY: MUTAGEN
<222> LOCATION: (1)..(1)
<223> OTHER INFORMATION: Xaa is L, S, W, G, A or K
<220> FEATURE:
<221> NAME/KEY: MUTAGEN
<222> LOCATION: (2)..(2)
<223> OTHER INFORMATION: Xaa is G, A or L

<400> SEQUENCE: 8

Xaa Xaa Ser
1

<210> SEQ ID NO 9
<211> LENGTH: 9
<212> TYPE: PRT
<213> ORGANISM: Artificial Sequence
<220> FEATURE:
<223> OTHER INFORMATION: LCDR3
<220> FEATURE:
<221> NAME/KEY: MUTAGEN
<222> LOCATION: (1)..(1)
<223> OTHER INFORMATION: Xaa is M, Q or L
<220> FEATURE:
<221> NAME/KEY: MUTAGEN
<222> LOCATION: (2)..(2)
<223> OTHER INFORMATION: Xaa is Q, G or H
<220> FEATURE:
<221> NAME/KEY: MUTAGEN
<222> LOCATION: (3)..(3)
<223> OTHER INFORMATION: Xaa is A, S, Y, R or H
<220> FEATURE:
<221> NAME/KEY: MUTAGEN
<222> LOCATION: (4)..(4)
<223> OTHER INFORMATION: Xaa is L, F, Y, T or N
<220> FEATURE:
<221> NAME/KEY: MUTAGEN
<222> LOCATION: (5)..(5)
<223> OTHER INFORMATION: Xaa is Q, S, R, I or H
<220> FEATURE:
<221> NAME/KEY: MUTAGEN
<222> LOCATION: (6)..(6)
<223> OTHER INFORMATION: Xaa is T, I, P, V, W or Y
```

```
<220> FEATURE:
<221> NAME/KEY: MUTAGEN
<222> LOCATION: (7)..(7)
<223> OTHER INFORMATION: Xaa is P or L
<220> FEATURE:
<221> NAME/KEY: MUTAGEN
<222> LOCATION: (8)..(8)
<223> OTHER INFORMATION: Xaa is Y, F, L or P
<220> FEATURE:
<221> NAME/KEY: MUTAGEN
<222> LOCATION: (9)..(9)
<223> OTHER INFORMATION: Xaa is T or I

<400> SEQUENCE: 9

Xaa Xaa Xaa Xaa Xaa Xaa Xaa Xaa Xaa
1               5

<210> SEQ ID NO 10
<211> LENGTH: 126
<212> TYPE: PRT
<213> ORGANISM: Artificial Sequence
<220> FEATURE:
<223> OTHER INFORMATION: VH

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Met His Trp Val Arg Gln Gly Thr Gly Lys Gly Leu Glu Trp Val
            35                  40                  45

Ser Gly Ile Gly Thr Ser Gly Asp Thr Tyr Tyr Pro Asp Ser Val Lys
        50                  55                  60

Gly Arg Phe Thr Ile Ser Arg Glu Asn Ala Lys Asn Ser Leu Asn Leu
65                  70                  75                  80

Gln Met Asn Ser Leu Arg Asp Gly Asp Thr Ala Met Tyr Tyr Cys Ala
                85                  90                  95

Arg Gly Pro Tyr Tyr Tyr Asn Ser Ser Gly Tyr Tyr Ser Tyr Asp Ala
            100                 105                 110

Leu Asp Ile Trp Gly Gln Gly Thr Met Val Thr Val Thr Ser
        115                 120                 125

<210> SEQ ID NO 11
<211> LENGTH: 112
<212> TYPE: PRT
<213> ORGANISM: Artificial Sequence
<220> FEATURE:
<223> OTHER INFORMATION: VL

<400> SEQUENCE: 11

Asp Ile Val Met Thr Gln Ser Pro Leu Ser Leu Ser Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Gly Val Gly Val Tyr Tyr Cys Met Gln Ala
                85                  90                  95
```

```
Leu Gln Thr Pro Tyr Thr Phe Gly Gln Gly Thr Lys Leu Glu Ile Lys
          100               105              110

<210> SEQ ID NO 12
<211> LENGTH: 8
<212> TYPE: PRT
<213> ORGANISM: Artificial Sequence
<220> FEATURE:
<223> OTHER INFORMATION: HCDR1

<400> SEQUENCE: 12

Gly Phe Thr Phe Ser Tyr Tyr Asp
1               5

<210> SEQ ID NO 13
<211> LENGTH: 7
<212> TYPE: PRT
<213> ORGANISM: Artificial Sequence
<220> FEATURE:
<223> OTHER INFORMATION: HCDR2

<400> SEQUENCE: 13

Ile Gly Thr Ser Gly Asp Thr
1               5

<210> SEQ ID NO 14
<211> LENGTH: 20
<212> TYPE: PRT
<213> ORGANISM: Artificial Sequence
<220> FEATURE:
<223> OTHER INFORMATION: HCDR3

<400> SEQUENCE: 14

Ala Arg Gly Pro Tyr Tyr Tyr Asn Ser Ser Gly Tyr Tyr Ser Tyr Asp
1               5                  10                  15

Ala Leu Asp Ile
          20

<210> SEQ ID NO 15
<211> LENGTH: 11
<212> TYPE: PRT
<213> ORGANISM: Artificial Sequence
<220> FEATURE:
<223> OTHER INFORMATION: LCDR1

<400> SEQUENCE: 15

Gln Ser Leu Leu His Ser Asn Gly Tyr Asn Tyr
1               5                  10

<210> SEQ ID NO 16
<211> LENGTH: 3
<212> TYPE: PRT
<213> ORGANISM: Artificial Sequence
<220> FEATURE:
<223> OTHER INFORMATION: LCDR2

<400> SEQUENCE: 16

Leu Gly Ser
1

<210> SEQ ID NO 17
<211> LENGTH: 9
<212> TYPE: PRT
<213> ORGANISM: Artificial Sequence
<220> FEATURE:
<223> OTHER INFORMATION: LCDR3
```

<400> SEQUENCE: 17

Met Gln Ala Leu Gln Thr Pro Tyr Thr
1               5

<210> SEQ ID NO 18
<211> LENGTH: 117
<212> TYPE: PRT
<213> ORGANISM: Artificial Sequence
<220> FEATURE:
<223> OTHER INFORMATION: VH

<400> SEQUENCE: 18

Glu Val Gln Leu Val Glu Ser Gly Gly Gly Leu Val Gln Pro Gly Arg
1               5                   10                  15

Ser Leu Arg Ile Ser Cys Ala Gly Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Asp Thr Ile Ala Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Val Ser Gly Ala Val Phe Asp Tyr Cys Gly Gln Gly Thr Gln
            100                 105                 110

Val Thr Val Ser Ser
        115

<210> SEQ ID NO 19
<211> LENGTH: 107
<212> TYPE: PRT
<213> ORGANISM: Artificial Sequence
<220> FEATURE:
<223> OTHER INFORMATION: VL

<400> SEQUENCE: 19

Asp Ile Gln Met Thr Gln Ser Pro Ser Ser Leu Ser Ala Ser Val Lys
1               5                   10                  15

Asp Arg Val Ile Ile Thr Cys Arg Ala Ser Gln Ser Ile His Ser Tyr
                20                  25                  30

Leu Asn Trp Tyr Gln Gln Lys Pro Gly Lys Ala Pro Lys Leu Leu Ile
            35                  40                  45

Tyr Ser Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Ile Pro Tyr
                85                  90                  95

Thr Phe Gly Gln Gly Thr Lys Leu Glu Ile Lys
            100                 105

<210> SEQ ID NO 20
<211> LENGTH: 8
<212> TYPE: PRT
<213> ORGANISM: Artificial Sequence
<220> FEATURE:
<223> OTHER INFORMATION: HCDR1

```
<400> SEQUENCE: 20

Gly Phe Thr Phe Asp Asp Tyr Ala
1               5

<210> SEQ ID NO 21
<211> LENGTH: 8
<212> TYPE: PRT
<213> ORGANISM: Artificial Sequence
<220> FEATURE:
<223> OTHER INFORMATION: HCDR2

<400> SEQUENCE: 21

Ile Ser Trp Asn Ser Asp Thr Ile
1               5

<210> SEQ ID NO 22
<211> LENGTH: 10
<212> TYPE: PRT
<213> ORGANISM: Artificial Sequence
<220> FEATURE:
<223> OTHER INFORMATION: HCDR3

<400> SEQUENCE: 22

Ala Lys Val Ser Gly Ala Val Phe Asp Tyr
1               5                   10

<210> SEQ ID NO 23
<211> LENGTH: 6
<212> TYPE: PRT
<213> ORGANISM: Artificial Sequence
<220> FEATURE:
<223> OTHER INFORMATION: LCDR1

<400> SEQUENCE: 23

Gln Ser Ile His Ser Tyr
1               5

<210> SEQ ID NO 24
<211> LENGTH: 3
<212> TYPE: PRT
<213> ORGANISM: Artificial Sequence
<220> FEATURE:
<223> OTHER INFORMATION: LCDR2

<400> SEQUENCE: 24

Ser Ala Ser
1

<210> SEQ ID NO 25
<211> LENGTH: 9
<212> TYPE: PRT
<213> ORGANISM: Artificial Sequence
<220> FEATURE:
<223> OTHER INFORMATION: LCDR3

<400> SEQUENCE: 25

Gln Gln Ser Phe Ser Ile Pro Tyr Thr
1               5

<210> SEQ ID NO 26
<211> LENGTH: 126
<212> TYPE: PRT
<213> ORGANISM: Artificial Sequence
<220> FEATURE:
<223> OTHER INFORMATION: VH

<400> SEQUENCE: 26
```

-continued

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Thr Gly Asn Gly Asn Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Ile Thr Gly Asn Ile Phe Tyr Tyr Tyr Tyr Tyr
            100                 105                 110

Met Asp Val Trp Gly Lys Gly Thr Thr Val Thr Val Ala Ser
        115                 120                 125

<210> SEQ ID NO 27
<211> LENGTH: 113
<212> TYPE: PRT
<213> ORGANISM: Artificial Sequence
<220> FEATURE:
<223> OTHER INFORMATION: VL

<400> SEQUENCE: 27

Asp Ile Val Val Thr Gln Ser Pro Asp Ser Leu Ala Val Ser Leu Gly
1               5                   10                  15

Glu Arg Ala Thr Ile Asn Cys Lys Ser Ser Gln Ser Phe Leu Ser Ser
                20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ile Pro Phe Thr Phe Gly Pro Gly Thr Lys Val Asp Ile
            100                 105                 110

Lys

<210> SEQ ID NO 28
<211> LENGTH: 8
<212> TYPE: PRT
<213> ORGANISM: Artificial Sequence
<220> FEATURE:
<223> OTHER INFORMATION: HCDR1

<400> SEQUENCE: 28

Gly Tyr Thr Phe Thr Ser Tyr Ala
1               5

<210> SEQ ID NO 29
<211> LENGTH: 8
<212> TYPE: PRT
<213> ORGANISM: Artificial Sequence
<220> FEATURE:
<223> OTHER INFORMATION: HCDR2
```

-continued

```
<400> SEQUENCE: 29

Ile Asn Thr Gly Asn Gly Asn Thr
1               5

<210> SEQ ID NO 30
<211> LENGTH: 19
<212> TYPE: PRT
<213> ORGANISM: Artificial Sequence
<220> FEATURE:
<223> OTHER INFORMATION: HCDR3

<400> SEQUENCE: 30

Ala Arg Gly Gly Ser Ile Thr Gly Asn Ile Phe Tyr Tyr Tyr Tyr Tyr
1               5                   10                  15

Met Asp Val

<210> SEQ ID NO 31
<211> LENGTH: 12
<212> TYPE: PRT
<213> ORGANISM: Artificial Sequence
<220> FEATURE:
<223> OTHER INFORMATION: LCDR1

<400> SEQUENCE: 31

Gln Ser Phe Leu Ser Ser Ser Asn Asn Lys Asn Tyr
1               5                   10

<210> SEQ ID NO 32
<211> LENGTH: 3
<212> TYPE: PRT
<213> ORGANISM: Artificial Sequence
<220> FEATURE:
<223> OTHER INFORMATION: LCDR2

<400> SEQUENCE: 32

Trp Ala Ser
1

<210> SEQ ID NO 33
<211> LENGTH: 9
<212> TYPE: PRT
<213> ORGANISM: Artificial Sequence
<220> FEATURE:
<223> OTHER INFORMATION: LCDR3

<400> SEQUENCE: 33

Gln Gln Tyr Tyr Ser Ile Pro Phe Thr
1               5

<210> SEQ ID NO 34
<211> LENGTH: 118
<212> TYPE: PRT
<213> ORGANISM: Artificial Sequence
<220> FEATURE:
<223> OTHER INFORMATION: VH

<400> SEQUENCE: 34

Glu Val Gln Leu Val Glu Ser Gly Gly Gly Leu Val Gln Pro Gly Arg
1               5                   10                  15

Ser Leu Arg Leu Ser Cys Glu Ala Ser Gly Phe Thr Phe Asp Asp Tyr
            20                  25                  30

Ala Met His Trp Val Arg Gln Pro Pro Gly Lys Gly Leu Glu Trp Val
        35                  40                  45

Ser Gly Ile Ser Trp Asn Ser Asp Asn Ile Gly Tyr Ala Asp Ser Val
```

```
          50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ile Gln Ser Gly Ser Ser Phe Asp Tyr Trp Gly Gln Gly Thr
                100                 105                 110

Leu Val Thr Val Ser Ser
        115

<210> SEQ ID NO 35
<211> LENGTH: 107
<212> TYPE: PRT
<213> ORGANISM: Artificial Sequence
<220> FEATURE:
<223> OTHER INFORMATION: VL

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ile Asn Phe
                20                  25                  30

Leu Asn Trp Tyr Gln Gln Lys Pro Gly Lys Ala Pro Lys Leu Leu Ile
            35                  40                  45

Tyr Gly Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Cys Cys Gln Gln Ser Ser Ser Ile Pro Leu
                85                  90                  95

Thr Phe Gly Gly Gly Thr Lys Val Glu Ile Lys
            100                 105

<210> SEQ ID NO 36
<211> LENGTH: 8
<212> TYPE: PRT
<213> ORGANISM: Artificial Sequence
<220> FEATURE:
<223> OTHER INFORMATION: HCDR1

<400> SEQUENCE: 36

Gly Phe Thr Phe Asp Asp Tyr Ala
1               5

<210> SEQ ID NO 37
<211> LENGTH: 8
<212> TYPE: PRT
<213> ORGANISM: Artificial Sequence
<220> FEATURE:
<223> OTHER INFORMATION: HCDR2

<400> SEQUENCE: 37

Ile Ser Trp Asn Ser Asp Asn Ile
1               5

<210> SEQ ID NO 38
<211> LENGTH: 11
<212> TYPE: PRT
<213> ORGANISM: Artificial Sequence
<220> FEATURE:
<223> OTHER INFORMATION: HCDR3
```

-continued

```
<400> SEQUENCE: 38

Ala Lys Ile Gln Ser Gly Ser Ser Phe Asp Tyr
1               5                   10

<210> SEQ ID NO 39
<211> LENGTH: 6
<212> TYPE: PRT
<213> ORGANISM: Artificial Sequence
<220> FEATURE:
<223> OTHER INFORMATION: LCDR1

<400> SEQUENCE: 39

Gln Ser Ile Ile Asn Phe
1               5

<210> SEQ ID NO 40
<211> LENGTH: 3
<212> TYPE: PRT
<213> ORGANISM: Artificial Sequence
<220> FEATURE:
<223> OTHER INFORMATION: LCDR2

<400> SEQUENCE: 40

Gly Ala Ser
1

<210> SEQ ID NO 41
<211> LENGTH: 9
<212> TYPE: PRT
<213> ORGANISM: Artificial Sequence
<220> FEATURE:
<223> OTHER INFORMATION: LCDR3

<400> SEQUENCE: 41

Gln Gln Ser Ser Ser Ile Pro Leu Thr
1               5

<210> SEQ ID NO 42
<211> LENGTH: 117
<212> TYPE: PRT
<213> ORGANISM: Artificial Sequence
<220> FEATURE:
<223> OTHER INFORMATION: VH

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Phe Asp Asp Cys
            20                  25                  30

Ala Met His Trp Val Arg Gln Thr Pro Gly Lys Gly Leu Glu Trp Val
        35                  40                  45

Ser Gly Ile Ser Trp Asn Ser Asp Thr Met Gly Tyr Ala Asp Ser Val
    50                  55                  60

Lys Gly Arg Phe Ile Ile Ser Arg Asp Asn Ala Lys Asn Ser Leu Tyr
65                  70                  75                  80

Leu Gln Met Asn Ser Leu Arg Val Glu Asp Thr Ala Leu Tyr His Cys
                85                  90                  95

Thr Arg Val Arg Ala Ala Val Phe Asp Tyr Trp Gly Gln Gly Val Leu
            100                 105                 110

Val Thr Val Ser Ser
        115
```

```
<210> SEQ ID NO 43
<211> LENGTH: 107
<212> TYPE: PRT
<213> ORGANISM: Artificial Sequence
<220> FEATURE:
<223> OTHER INFORMATION: VL

<400> SEQUENCE: 43

Asp Ile His Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Phe Gln Gln Lys Pro Gly Lys Ala Pro Thr Val Leu Ile
        35                  40                  45

Tyr Ala Ala Ser Ser Leu Gln Ser Gly Val Ser Ser Arg Phe Ser Gly
    50                  55                  60

Arg Gly Ser Gly Ala Asp Phe Thr Leu Thr Ile Ser Ser Leu Gln Pro
65                  70                  75                  80

Glu Asp Phe Ala Ser Tyr Phe Cys Gln Gln Ser Phe Ser Pro Leu Tyr
                85                  90                  95

Ile Phe Gly Gln Gly Thr Lys Val Glu Ile Lys
            100                 105

<210> SEQ ID NO 44
<211> LENGTH: 8
<212> TYPE: PRT
<213> ORGANISM: Artificial Sequence
<220> FEATURE:
<223> OTHER INFORMATION: HCDR1

<400> SEQUENCE: 44

Gly Phe Thr Phe Asp Asp Cys Ala
1               5

<210> SEQ ID NO 45
<211> LENGTH: 8
<212> TYPE: PRT
<213> ORGANISM: Artificial Sequence
<220> FEATURE:
<223> OTHER INFORMATION: HCDR2

<400> SEQUENCE: 45

Ile Ser Trp Asn Ser Asp Thr Met
1               5

<210> SEQ ID NO 46
<211> LENGTH: 10
<212> TYPE: PRT
<213> ORGANISM: Artificial Sequence
<220> FEATURE:
<223> OTHER INFORMATION: HCDR3

<400> SEQUENCE: 46

Thr Arg Val Arg Ala Ala Val Phe Asp Tyr
1               5                   10

<210> SEQ ID NO 47
<211> LENGTH: 6
<212> TYPE: PRT
<213> ORGANISM: Artificial Sequence
<220> FEATURE:
<223> OTHER INFORMATION: LCDR1

<400> SEQUENCE: 47
```

```
Gln Ser Ile Ser Ser Tyr
1               5

<210> SEQ ID NO 48
<211> LENGTH: 3
<212> TYPE: PRT
<213> ORGANISM: Artificial Sequence
<220> FEATURE:
<223> OTHER INFORMATION: LCDR2

<400> SEQUENCE: 48

Ala Ala Ser
1

<210> SEQ ID NO 49
<211> LENGTH: 9
<212> TYPE: PRT
<213> ORGANISM: Artificial Sequence
<220> FEATURE:
<223> OTHER INFORMATION: LCDR3

<400> SEQUENCE: 49

Gln Gln Ser Phe Ser Pro Leu Tyr Ile
1               5

<210> SEQ ID NO 50
<211> LENGTH: 126
<212> TYPE: PRT
<213> ORGANISM: Artificial Sequence
<220> FEATURE:
<223> OTHER INFORMATION: VH

<400> SEQUENCE: 50

Gln Val Gln Leu Val Gln Ser Gly Ala Glu Val Lys Lys Pro Gly Ala
1               5                   10                  15

Ser Ala Lys Val Ser Cys Lys Ala Ser Gly Tyr Thr Phe Thr Ser Tyr
                20                  25                  30

Ala Met Gln Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Leu Glu Leu Asp Ile Tyr Tyr Tyr Phe Tyr Tyr
            100                 105                 110

Met Asp Val Trp Gly Lys Gly Thr Thr Val Thr Val Ser Ser
        115                 120                 125

<210> SEQ ID NO 51
<211> LENGTH: 113
<212> TYPE: PRT
<213> ORGANISM: Artificial Sequence
<220> FEATURE:
<223> OTHER INFORMATION: VL

<400> SEQUENCE: 51

Asp Ile Val Met Ser Gln Ser Pro Asp Ser Leu Ala Val Ser Leu Gly
1               5                   10                  15

Glu Arg Thr Thr Ile Asn Cys Lys Ser Ser Gln Ser Val Leu His Ser
                20                  25                  30
```

-continued

```
Ser Gln Asn Lys Asn Tyr Leu Ala Trp Tyr Gln Gln Lys Pro Gly Gln
        35                  40                  45

Pro Pro Asn Pro Leu Ile His Trp Ala Ser Thr Arg Glu Ser Gly Val
        50                  55                  60

Pro Asp Arg Phe Ser Gly Ser Gly Ser Gly Thr Asp Phe Thr Leu Thr
65                      70                  75                  80

Ile Ser Ser Leu Gln Ala Glu Asp Val Ala Val Tyr Tyr Cys Gln Gln
                85                  90                  95

Tyr Tyr Arg Val Pro Phe Thr Phe Gly Pro Gly Thr Lys Val Asp Ile
                100                 105                 110

Lys

<210> SEQ ID NO 52
<211> LENGTH: 8
<212> TYPE: PRT
<213> ORGANISM: Artificial Sequence
<220> FEATURE:
<223> OTHER INFORMATION: HCDR1

<400> SEQUENCE: 52

Gly Tyr Thr Phe Thr Ser Tyr Ala
1               5

<210> SEQ ID NO 53
<211> LENGTH: 8
<212> TYPE: PRT
<213> ORGANISM: Artificial Sequence
<220> FEATURE:
<223> OTHER INFORMATION: HCDR2

<400> SEQUENCE: 53

Ile Asn Ala Gly Asn Gly Asn Thr
1               5

<210> SEQ ID NO 54
<211> LENGTH: 19
<212> TYPE: PRT
<213> ORGANISM: Artificial Sequence
<220> FEATURE:
<223> OTHER INFORMATION: HCDR3

<400> SEQUENCE: 54

Ala Arg Gly Gly Arg Leu Glu Leu Asp Ile Tyr Tyr Tyr Phe Tyr Tyr
1               5                   10                  15

Met Asp Val

<210> SEQ ID NO 55
<211> LENGTH: 12
<212> TYPE: PRT
<213> ORGANISM: Artificial Sequence
<220> FEATURE:
<223> OTHER INFORMATION: LCDR1

<400> SEQUENCE: 55

Gln Ser Val Leu His Ser Ser Gln Asn Lys Asn Tyr
1               5                   10

<210> SEQ ID NO 56
<211> LENGTH: 3
<212> TYPE: PRT
<213> ORGANISM: Artificial Sequence
<220> FEATURE:
<223> OTHER INFORMATION: LCDR2
```

```
<400> SEQUENCE: 56

Trp Ala Ser
1

<210> SEQ ID NO 57
<211> LENGTH: 9
<212> TYPE: PRT
<213> ORGANISM: Artificial Sequence
<220> FEATURE:
<223> OTHER INFORMATION: LCDR3

<400> SEQUENCE: 57

Gln Gln Tyr Tyr Arg Val Pro Phe Thr
1               5

<210> SEQ ID NO 58
<211> LENGTH: 117
<212> TYPE: PRT
<213> ORGANISM: Artificial Sequence
<220> FEATURE:
<223> OTHER INFORMATION: VH

<400> SEQUENCE: 58

Glu Val Arg Leu Val Glu Ser Gly Gly Gly Leu Val Gln Pro Gly Arg
1               5                   10                  15

Ser Leu Arg Leu Ser Cys Ala Ala Ser Gly Phe Thr Ser Asn Asp Tyr
            20                  25                  30

Ala Met His Trp Val Arg Gln Ala Pro Gly Arg Gly Leu Glu Trp Val
        35                  40                  45

Ser Gly Ile Ser Trp Asn Ser Asp Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Thr Val Val Ser Ala Tyr Phe Asp Tyr Trp Gly Gln Gly Thr Leu
            100                 105                 110

Val Thr Val Ser Ser
        115

<210> SEQ ID NO 59
<211> LENGTH: 107
<212> TYPE: PRT
<213> ORGANISM: Artificial Sequence
<220> FEATURE:
<223> OTHER INFORMATION: VL

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gly Ser Tyr Ile Ile Pro Leu
                85                  90                  95
```

```
Thr Phe Gly Gly Gly Thr Arg Val Glu Ile Lys
            100                 105

<210> SEQ ID NO 60
<211> LENGTH: 8
<212> TYPE: PRT
<213> ORGANISM: Artificial Sequence
<220> FEATURE:
<223> OTHER INFORMATION: HCDR1

<400> SEQUENCE: 60

Gly Phe Thr Ser Asn Asp Tyr Ala
1               5

<210> SEQ ID NO 61
<211> LENGTH: 8
<212> TYPE: PRT
<213> ORGANISM: Artificial Sequence
<220> FEATURE:
<223> OTHER INFORMATION: HCDR2

<400> SEQUENCE: 61

Ile Ser Trp Asn Ser Asp Ser Ile
1               5

<210> SEQ ID NO 62
<211> LENGTH: 10
<212> TYPE: PRT
<213> ORGANISM: Artificial Sequence
<220> FEATURE:
<223> OTHER INFORMATION: HCDR3

<400> SEQUENCE: 62

Ala Thr Val Val Ser Ala Tyr Phe Asp Tyr
1               5                   10

<210> SEQ ID NO 63
<211> LENGTH: 6
<212> TYPE: PRT
<213> ORGANISM: Artificial Sequence
<220> FEATURE:
<223> OTHER INFORMATION: LCDR1

<400> SEQUENCE: 63

Gln Ser Ile Ser Thr Tyr
1               5

<210> SEQ ID NO 64
<211> LENGTH: 3
<212> TYPE: PRT
<213> ORGANISM: Artificial Sequence
<220> FEATURE:
<223> OTHER INFORMATION: LCDR2

<400> SEQUENCE: 64

Ala Ala Ser
1

<210> SEQ ID NO 65
<211> LENGTH: 9
<212> TYPE: PRT
<213> ORGANISM: Artificial Sequence
<220> FEATURE:
<223> OTHER INFORMATION: LCDR3

<400> SEQUENCE: 65
```

-continued

```
Gln Gly Ser Tyr Ile Ile Pro Leu Thr
1               5

<210> SEQ ID NO 66
<211> LENGTH: 121
<212> TYPE: PRT
<213> ORGANISM: Artificial Sequence
<220> FEATURE:
<223> OTHER INFORMATION: VH

<400> SEQUENCE: 66

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Leu His Trp Val Arg Gln Ser Pro Gly His Gly Leu Glu Trp Met
        35                  40                  45

Gly Arg Ile Tyr Pro Asn Ser Gly Asp Thr Asn Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Leu Tyr Tyr Cys
                85                  90                  95

Ala Arg Gly Phe Asn Trp Asn Tyr Glu Gly Gly Phe Asp Ile Trp Gly
            100                 105                 110

Gln Gly Thr Met Val Thr Val Ser Ser
        115                 120

<210> SEQ ID NO 67
<211> LENGTH: 112
<212> TYPE: PRT
<213> ORGANISM: Artificial Sequence
<220> FEATURE:
<223> OTHER INFORMATION: VL

<400> SEQUENCE: 67

Asp Val Val Met Thr Gln Ser Pro Leu Ser Leu Ser Val Thr Leu Gly
1               5                   10                  15

Gln Pro Ala Ser Ile Ser Cys Arg Ser Gly Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Leu Ser Ser Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Met Glu Ala Glu Asp Val Gly Val Tyr Tyr Cys Met Gln Arg
                85                  90                  95

Thr His Trp Pro Pro Thr Phe Gly Gln Gly Thr Lys Val Glu Ile Lys
            100                 105                 110

<210> SEQ ID NO 68
<211> LENGTH: 8
<212> TYPE: PRT
<213> ORGANISM: Artificial Sequence
<220> FEATURE:
<223> OTHER INFORMATION: HCDR1

<400> SEQUENCE: 68

Gly Tyr Thr Phe Thr Ala Tyr Tyr
```

```
1               5

<210> SEQ ID NO 69
<211> LENGTH: 8
<212> TYPE: PRT
<213> ORGANISM: Artificial Sequence
<220> FEATURE:
<223> OTHER INFORMATION: HCDR2

<400> SEQUENCE: 69

Ile Tyr Pro Asn Ser Gly Asp Thr
1               5

<210> SEQ ID NO 70
<211> LENGTH: 14
<212> TYPE: PRT
<213> ORGANISM: Artificial Sequence
<220> FEATURE:
<223> OTHER INFORMATION: HCDR3

<400> SEQUENCE: 70

Ala Arg Gly Phe Asn Trp Asn Tyr Glu Gly Gly Phe Asp Ile
1               5                   10

<210> SEQ ID NO 71
<211> LENGTH: 11
<212> TYPE: PRT
<213> ORGANISM: Artificial Sequence
<220> FEATURE:
<223> OTHER INFORMATION: LCDR1

<400> SEQUENCE: 71

Gln Ser Leu Val Tyr Ser Asp Gly Asn Thr Tyr
1               5                   10

<210> SEQ ID NO 72
<211> LENGTH: 3
<212> TYPE: PRT
<213> ORGANISM: Artificial Sequence
<220> FEATURE:
<223> OTHER INFORMATION: LCDR2

<400> SEQUENCE: 72

Lys Leu Ser
1

<210> SEQ ID NO 73
<211> LENGTH: 9
<212> TYPE: PRT
<213> ORGANISM: Artificial Sequence
<220> FEATURE:
<223> OTHER INFORMATION: LCDR3

<400> SEQUENCE: 73

Met Gln Arg Thr His Trp Pro Pro Thr
1               5

<210> SEQ ID NO 74
<211> LENGTH: 126
<212> TYPE: PRT
<213> ORGANISM: Artificial Sequence
<220> FEATURE:
<223> OTHER INFORMATION: VH

<400> SEQUENCE: 74

Gln Val Gln Leu Val Gln Ser Gly Ala Glu Val Lys Lys Pro Gly Ala
1               5                   10                  15
```

-continued

Ser Ala Lys Val Ser Cys Lys Ala Ser Gly Tyr Thr Phe Thr Ser Tyr
            20                  25                  30

Ala Met Gln Trp Val Arg Gln Ala Pro Gly Gln Arg Leu Glu Trp Met
            35                  40                  45

Gly Trp Ile Asn Ala Gly Asn Gly Asn Ile Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Leu Glu Leu Asp Val Tyr Tyr Tyr Phe Tyr Tyr
            100                 105                 110

Met Asp Val Trp Gly Lys Gly Thr Thr Val Thr Val Ser Ser
        115                 120                 125

<210> SEQ ID NO 75
<211> LENGTH: 113
<212> TYPE: PRT
<213> ORGANISM: Artificial Sequence
<220> FEATURE:
<223> OTHER INFORMATION: VL

<400> SEQUENCE: 75

Asp Ile Val Met Ser Gln Ser Pro Asp Ser Leu Ala Val Ser Leu Gly
1               5                   10                  15

Glu Arg Thr Thr Ile Asn Cys Lys Ser Ser Gln Ser Val Leu His Ser
            20                  25                  30

Ser Gln Asn Lys Asn Tyr Leu Ala Trp Tyr Gln Gln Lys Pro Gly Gln
        35                  40                  45

Pro Pro Asn Pro Leu Ile His Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Val Pro Phe Thr Phe Gly Pro Gly Thr Lys Val Asp Ile
            100                 105                 110

Lys

<210> SEQ ID NO 76
<211> LENGTH: 8
<212> TYPE: PRT
<213> ORGANISM: Artificial Sequence
<220> FEATURE:
<223> OTHER INFORMATION: HCDR1

<400> SEQUENCE: 76

Gly Tyr Thr Phe Thr Ser Tyr Ala
1               5

<210> SEQ ID NO 77
<211> LENGTH: 8
<212> TYPE: PRT
<213> ORGANISM: Artificial Sequence
<220> FEATURE:
<223> OTHER INFORMATION: HCDR2

<400> SEQUENCE: 77

Ile Asn Ala Gly Asn Gly Asn Ile

-continued 1                          5

<210> SEQ ID NO 78
<211> LENGTH: 19
<212> TYPE: PRT
<213> ORGANISM: Artificial Sequence
<220> FEATURE:
<223> OTHER INFORMATION: HCDR3

<400> SEQUENCE: 78

Ala Arg Gly Gly Arg Leu Glu Leu Asp Val Tyr Tyr Tyr Phe Tyr Tyr
1                          5                          10                         15

Met Asp Val

<210> SEQ ID NO 79
<211> LENGTH: 12
<212> TYPE: PRT
<213> ORGANISM: Artificial Sequence
<220> FEATURE:
<223> OTHER INFORMATION: LCDR1

<400> SEQUENCE: 79

Gln Ser Val Leu His Ser Ser Gln Asn Lys Asn Tyr
1                          5                          10

<210> SEQ ID NO 80
<211> LENGTH: 3
<212> TYPE: PRT
<213> ORGANISM: Artificial Sequence
<220> FEATURE:
<223> OTHER INFORMATION: LCDR2

<400> SEQUENCE: 80

Trp Ala Ser
1

<210> SEQ ID NO 81
<211> LENGTH: 9
<212> TYPE: PRT
<213> ORGANISM: Artificial Sequence
<220> FEATURE:
<223> OTHER INFORMATION: LCDR3

<400> SEQUENCE: 81

Gln Gln Tyr Tyr Arg Val Pro Phe Thr
1                          5

<210> SEQ ID NO 82
<211> LENGTH: 119
<212> TYPE: PRT
<213> ORGANISM: Artificial Sequence
<220> FEATURE:
<223> OTHER INFORMATION: VH

<400> SEQUENCE: 82

Glu Val Gln Leu Val Glu Ser Gly Gly Gly Leu Val Gln Pro Gly Arg
1                          5                          10                         15

Ser Leu Arg Leu Ser Cys Ala Ala Ser Gly Phe Thr Phe Ala Asp His
                    20                          25                          30

Ala Met His Trp Val Arg Gln Ala Pro Gly Lys Gly Leu Glu Trp Val
                    35                          40                          45

Ser Gly Ile Ser Trp Asn Ser Asp His Ile Gly Tyr Ala Asp Ser Val
          50                          55                          60

Lys Gly Arg Phe Thr Ile Ser Arg Asp Asn Ala Lys Asn Ser Leu Tyr

-continued

```
65                    70                    75                    80

Leu Gln Met Asn Ser Leu Arg Pro Glu Asp Thr Ala Leu Tyr Tyr Cys
                85                    90                    95

Ala Lys Asp Ile Phe Ser Pro Thr Gly Asp Gly Tyr Trp Gly Gln Gly
            100                   105                   110

Thr Leu Val Thr Val Ser Ser
        115

<210> SEQ ID NO 83
<211> LENGTH: 107
<212> TYPE: PRT
<213> ORGANISM: Artificial Sequence
<220> FEATURE:
<223> OTHER INFORMATION: VL

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asn
                20                  25                  30

Leu Gly Trp Phe Gln Gln Lys Pro Gly Lys Thr Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Ile Ile Ser Ser Leu Gln Pro
65                  70                  75                  80

Glu Asp Phe Ala Thr Tyr Tyr Cys Leu His His Asn Ser Tyr Pro Pro
                85                  90                  95

Thr Phe Gly Gln Gly Thr Lys Val Glu Ile Lys
            100                 105

<210> SEQ ID NO 84
<211> LENGTH: 8
<212> TYPE: PRT
<213> ORGANISM: Artificial Sequence
<220> FEATURE:
<223> OTHER INFORMATION: HCDR1

<400> SEQUENCE: 84

Gly Phe Thr Phe Ala Asp His Ala
1               5

<210> SEQ ID NO 85
<211> LENGTH: 8
<212> TYPE: PRT
<213> ORGANISM: Artificial Sequence
<220> FEATURE:
<223> OTHER INFORMATION: HCDR2

<400> SEQUENCE: 85

Ile Ser Trp Asn Ser Asp His Ile
1               5

<210> SEQ ID NO 86
<211> LENGTH: 12
<212> TYPE: PRT
<213> ORGANISM: Artificial Sequence
<220> FEATURE:
<223> OTHER INFORMATION: HCDR3

<400> SEQUENCE: 86

Ala Lys Asp Ile Phe Ser Pro Thr Gly Asp Gly Tyr
```

-continued

```
1               5                   10
```

<210> SEQ ID NO 87
<211> LENGTH: 6
<212> TYPE: PRT
<213> ORGANISM: Artificial Sequence
<220> FEATURE:
<223> OTHER INFORMATION: LCDR1

<400> SEQUENCE: 87

Gln Asp Ile Arg Asn Asn
1               5

<210> SEQ ID NO 88
<211> LENGTH: 3
<212> TYPE: PRT
<213> ORGANISM: Artificial Sequence
<220> FEATURE:
<223> OTHER INFORMATION: LCDR2

<400> SEQUENCE: 88

Ala Ala Ser
1

<210> SEQ ID NO 89
<211> LENGTH: 9
<212> TYPE: PRT
<213> ORGANISM: Artificial Sequence
<220> FEATURE:
<223> OTHER INFORMATION: LCDR3

<400> SEQUENCE: 89

Leu His His Asn Ser Tyr Pro Pro Thr
1               5

<210> SEQ ID NO 90
<211> LENGTH: 119
<212> TYPE: PRT
<213> ORGANISM: Artificial Sequence
<220> FEATURE:
<223> OTHER INFORMATION: VH

<400> SEQUENCE: 90

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp His
                20                  25                  30

Ala Met His Trp Val Arg Gln Ala Pro Gly Lys Gly Leu Glu Trp Val
        35                  40                  45

Ser Gly Ile Ser Trp Asn Ser Val His Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Phe Ser Pro Thr Gly Asp Asp Tyr Trp Gly Gln Gly
            100                 105                 110

Thr Leu Val Thr Val Ser Ser
        115

<210> SEQ ID NO 91
<211> LENGTH: 107
<212> TYPE: PRT
```

<213> ORGANISM: Artificial Sequence
<220> FEATURE:
<223> OTHER INFORMATION: VL

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asn
                20                  25                  30

Leu Gly Trp Phe Gln Gln Lys Pro Gly Lys Thr Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu His His Asn Ser Tyr Pro Pro
                85                  90                  95

Thr Phe Gly Gln Gly Thr Lys Val Glu Ile Lys
            100                 105

<210> SEQ ID NO 92
<211> LENGTH: 8
<212> TYPE: PRT
<213> ORGANISM: Artificial Sequence
<220> FEATURE:
<223> OTHER INFORMATION: HCDR1

<400> SEQUENCE: 92

Gly Phe Thr Phe Asp Asp His Ala
1               5

<210> SEQ ID NO 93
<211> LENGTH: 8
<212> TYPE: PRT
<213> ORGANISM: Artificial Sequence
<220> FEATURE:
<223> OTHER INFORMATION: HCDR2

<400> SEQUENCE: 93

Ile Ser Trp Asn Ser Val His Ile
1               5

<210> SEQ ID NO 94
<211> LENGTH: 12
<212> TYPE: PRT
<213> ORGANISM: Artificial Sequence
<220> FEATURE:
<223> OTHER INFORMATION: HCDR3

<400> SEQUENCE: 94

Ala Lys Asp Ile Phe Ser Pro Thr Gly Asp Asp Tyr
1               5                   10

<210> SEQ ID NO 95
<211> LENGTH: 6
<212> TYPE: PRT
<213> ORGANISM: Artificial Sequence
<220> FEATURE:
<223> OTHER INFORMATION: LCDR1

<400> SEQUENCE: 95

Gln Asp Ile Arg Asn Asn
1               5

-continued

<210> SEQ ID NO 96
<211> LENGTH: 3
<212> TYPE: PRT
<213> ORGANISM: Artificial Sequence
<220> FEATURE:
<223> OTHER INFORMATION: LCDR2

<400> SEQUENCE: 96

Ala Ala Ser
1

<210> SEQ ID NO 97
<211> LENGTH: 9
<212> TYPE: PRT
<213> ORGANISM: Artificial Sequence
<220> FEATURE:
<223> OTHER INFORMATION: LCDR3

<400> SEQUENCE: 97

Leu His His Asn Ser Tyr Pro Pro Thr
1               5

<210> SEQ ID NO 98
<211> LENGTH: 117
<212> TYPE: PRT
<213> ORGANISM: Artificial Sequence
<220> FEATURE:
<223> OTHER INFORMATION: VH

<400> SEQUENCE: 98

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Asp Asn Ile Ala Tyr Ala Asp Ser Val
    50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Thr Glu Asp Thr Ala Ile Tyr Tyr Cys
                85                  90                  95

Ala Lys Val Ala Ala Ala Thr Phe Asp Tyr Arg Gly Gln Gly Thr Leu
            100                 105                 110

Val Thr Val Ser Ser
        115

<210> SEQ ID NO 99
<211> LENGTH: 107
<212> TYPE: PRT
<213> ORGANISM: Artificial Sequence
<220> FEATURE:
<223> OTHER INFORMATION: VL

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

```
Phe Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Ser Cys Gln Gln Ser Phe Ser Ile Pro Phe
                85              90              95

Thr Phe Gly Pro Gly Thr Lys Val Asp Ile Lys
            100             105
```

<210> SEQ ID NO 100
<211> LENGTH: 8
<212> TYPE: PRT
<213> ORGANISM: Artificial Sequence
<220> FEATURE:
<223> OTHER INFORMATION: HCDR1

<400> SEQUENCE: 100

```
Gly Phe Thr Phe Asp Asp Tyr Ala
1               5
```

<210> SEQ ID NO 101
<211> LENGTH: 8
<212> TYPE: PRT
<213> ORGANISM: Artificial Sequence
<220> FEATURE:
<223> OTHER INFORMATION: HCDR2

<400> SEQUENCE: 101

```
Ile Ser Trp Asn Ser Asp Asn Ile
1               5
```

<210> SEQ ID NO 102
<211> LENGTH: 10
<212> TYPE: PRT
<213> ORGANISM: Artificial Sequence
<220> FEATURE:
<223> OTHER INFORMATION: HCDR3

<400> SEQUENCE: 102

```
Ala Lys Val Ala Ala Ala Thr Phe Asp Tyr
1               5               10
```

<210> SEQ ID NO 103
<211> LENGTH: 6
<212> TYPE: PRT
<213> ORGANISM: Artificial Sequence
<220> FEATURE:
<223> OTHER INFORMATION: LCDR1

<400> SEQUENCE: 103

```
Gln Ser Ile Ser Ser Tyr
1               5
```

<210> SEQ ID NO 104
<211> LENGTH: 3
<212> TYPE: PRT
<213> ORGANISM: Artificial Sequence
<220> FEATURE:
<223> OTHER INFORMATION: LCDR2

<400> SEQUENCE: 104

```
Ala Ala Ser
1
```

<210> SEQ ID NO 105

```
<211> LENGTH: 9
<212> TYPE: PRT
<213> ORGANISM: Artificial Sequence
<220> FEATURE:
<223> OTHER INFORMATION: LCDR3

<400> SEQUENCE: 105

Gln Gln Ser Phe Ser Ile Pro Phe Thr
1               5

<210> SEQ ID NO 106
<211> LENGTH: 330
<212> TYPE: PRT
<213> ORGANISM: Artificial Sequence
<220> FEATURE:
<223> OTHER INFORMATION: Heavy chain constant region

<400> SEQUENCE: 106

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
```

-continued

```
305               310               315               320

Gln Lys Ser Leu Ser Leu Ser Pro Gly Lys
                325               330

<210> SEQ ID NO 107
<211> LENGTH: 107
<212> TYPE: PRT
<213> ORGANISM: Artificial Sequence
<220> FEATURE:
<223> OTHER INFORMATION: Light chain constant region

<400> SEQUENCE: 107

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```